United States Patent
Kim et al.

(10) Patent No.: US 12,357,553 B2
(45) Date of Patent: Jul. 15, 2025

(54) COMPOSITION FOR TREATING HAIR LOSS OR PROMOTING HAIR GROWTH, COMPRISING PIPERONYLIC ACID

(71) Applicant: HESED BIO CO., LTD., Gyeongsangbuk-do (KR)

(72) Inventors: Kyong Tai Kim, Gyeongsangbuk-do (KR); Dohyun Lee, Gyeongsangbuk-do (KR); Jinsun Lim, Gyeongsangbuk-do (KR)

(73) Assignee: HESED BIO CO., LTD., Gyeongsangbuk-do (KR)

( * ) Notice: Subject to any disclaimer, the term of this patent is extended or adjusted under 35 U.S.C. 154(b) by 582 days.

(21) Appl. No.: 17/818,083

(22) Filed: Aug. 8, 2022

(65) Prior Publication Data
US 2022/0370320 A1    Nov. 24, 2022

Related U.S. Application Data

(63) Continuation-in-part of application No. 16/635,199, filed as application No. PCT/KR2018/008278 on Jul. 23, 2018, now Pat. No. 11,439,577.

(30) Foreign Application Priority Data

Aug. 2, 2017    (KR) ........................ 10-2017-0098011

(51) Int. Cl.
A61K 8/49    (2006.01)
A61K 8/04    (2006.01)
A61Q 5/00    (2006.01)
A61Q 7/00    (2006.01)

(52) U.S. Cl.
CPC ............ *A61K 8/4973* (2013.01); *A61K 8/042* (2013.01); *A61Q 5/00* (2013.01); *A61Q 7/00* (2013.01)

(58) Field of Classification Search
CPC ........... A61K 8/4973; A61Q 5/00; A61Q 7/00
See application file for complete search history.

(56) References Cited

U.S. PATENT DOCUMENTS

2021/0100728 A1    4/2021    Kim

FOREIGN PATENT DOCUMENTS

| EP | 0997137 A1 | 5/2000 |
|---|---|---|
| JP | 2002029957 A | 1/2002 |
| JP | 2005263638 A | 9/2005 |
| JP | 2007533313 | 11/2007 |
| KR | 100846125 B1 | 7/2008 |
| KR | 1020150018261 A | 2/2015 |
| KR | 101609041 | 4/2016 |
| WO | 2008035904 A1 | 3/2008 |
| WO | 2008146085 | 12/2008 |

OTHER PUBLICATIONS

European Patent Office Communication pursuant to Article 94(3) EPC issued in App. No. EP18841461, dated Oct. 20, 2022, 7 pages.
Lin L. et al., "Inhibitory effects of piperonylic acid on the excessive proliferation of vascular smooth muscle cells and luminal stenosis", vol. 115, No. 12 (2014), pp. 761-765.
Lee, D. et al., "Piperonylic acid stimulates keratinocyte growth and survival by activating epidermal growth factor receptor (EGFR)", Scientific Reports, Jan. 9, 2018, vol. 8(162), pp. 1-9.
"Innovation zone 2014—discover the latest ingredients and the most innovative beauty products" in-cosmetics, 2014, pp. 1-39.
Process Biochemistry. 2013, vol. 48, pp. 1706-1714 (Abstract).
European Journal of Medicinal Chemistry. 2014, vol. 71, pp. 1-14 (Abstract).

*Primary Examiner* — Sahar Javanmard
(74) *Attorney, Agent, or Firm* — Riverside Law LLP

(57) ABSTRACT

The present invention relates to a pharmaceutical composition comprising piperonylic acid as an effective ingredient for anti-aging or regenerating the skin. A composition according to the present invention utilizes piperonylic acid that various plant species naturally contain therein and thus does not cause side effects. Piperonylic acid activates signals associated with cell survival, growth, and proliferation to exhibit the effect of increasing the resistance and survival of skin cells against external stimuli and enhancing the regeneration of the skin damaged due to external stimuli or senescence. In addition, piperonylic acid of the present invention has a similar function to EGF, but is stable and small in size in contrast to EGF. Thus, piperonylic acid of the present invention has the advantage of being able to easily move to the skin basal layer across the skin barrier and perform its function. Piperonylic acid of the present invention is expected to find applications in various fields including medicines, quasi-drugs, cosmetics, cosmetic substances, functional biomaterials, and functional food materials. In addition, the present invention provides a use of piperonylic acid for preventing hair loss or promoting hair growth. Piperonylic acid is a component derived from natural products, is safe, has few side effects, and has an effect of effectively improving androgenic alopecia symptoms, and the like, and thus can be used in various applications such as a cosmetic, drug, quasi-drug or food for preventing hair loss or promoting hair growth.

10 Claims, 24 Drawing Sheets

FIG. 3B

| Top score \ PDB entry | Predicted binding site |
|---|---|
| | 1MOX (A.A. 25-525) |
| 1 | K25, C251, R255 |
| 2 | R334 |
| 3 | S286, G305 |
| 4 | Y270, P265 |
| 5 | Y270 |
| 6 | S286 |
| 7 | R108 |
| 8 | R255 |
| 9 | C311, E317 |
| 10 | L469 |

COMPOSITION FOR TREATING HAIR LOSS OR PROMOTING HAIR GROWTH, COMPRISING PIPERONYLIC ACID

CROSS-REFERENCE TO RELATED APPLICATIONS

This application is a continuation-in-part of U.S. application Ser. No. 16/635,199, filed Jan. 30, 2020, which is the U.S. national phase application filed under 35 U.S.C. § 371 claiming benefit to International Patent Application No. PCT/KR2018/008278, filed on Jul. 23, 2018, which claims priority to Korean Patent Application No. 10-2017-0098011, filed Aug. 2, 2017, the disclosures of which are incorporated herein by reference in their entirety.

TECHNICAL FIELD

The present invention relates to a pharmaceutical composition comprising piperonylic acid as an effective ingredient for anti-aging or regenerating the skin.

In addition, the present invention relates to a use of piperonylic acid for preventing hair loss or promoting hair growth.

BACKGROUND ART

Cell senescence is a physiological phenomenon that all living organisms cannot evade. Among them, skin senescence is very important for those who crave beauty. Due to skin senescence, the skin loses elasticity and becomes wrinkled, and senescence symptoms such as pigmentation and dermal atrophy appear. The skin senescence is largely divided into two types: physiological senescence, which exhibits changes in skin function, structure and shape, and senescence due to an external environment such as ultraviolet rays.

In addition to the deterioration in cell function with aging, the skin is affected by skin damage due to the external environment such as ultraviolet rays as follows. First, the division rate of keratinocytes divided in the epidermal basal layer slows down. The normal skin turnover period is about 28 days, but as senescence progresses, this cycle lengthens. Second, the number of fibroblasts in the dermis layer is reduced and the function thereof deteriorates. Fibroblasts are known to mainly produce collagen and elastin fibers that impart elasticity to the skin. However, when the number of fibroblasts in the dermis layer is reduced and the function thereof deteriorates, the biosynthesis of collagen and elastin fibers is reduced, and thus the atrophy of the dermis layer occurs. Third, the expression of matrix metalloproteinases is increased. Matrix metalloproteinases are enzymes that break down collagen and elastin fibers. While their expression increases with age, the atrophy of the dermis layer is further accelerated. In addition to this, skin senescence progresses in a very complex manner, while being affected by changes in immune responses, and the like.

As people's life expectancy increases and living standards rise, demand for substances that may nurture beauty increases while demands for well-being and beauty increase. As there is the saying that the most beautiful thing is youth, there is a need for developing an innovative substance that maintains the appearance of a youthful face by preventing and alleviating skin senescence.

Epidermal growth factor (EGF) is known as a growth factor that regulates the growth and survival of epidermal and epithelial cells. The discovery of EGF was an epoch-making event and was also selected for the Nobel Prize in Physiology or Medicine in 1986. EGF has been used medically to treat wounds of ulcers or burns that are difficult to heal depending on the function thereof, and recently has been widely used as a raw material of cosmetics for skin regeneration. However, EGF requires a lot of cost and labor for biosynthesis or separation and purification, and it is not easy to keep EGF in active state. Further, since EGF belongs to a relatively large polymer, there is a problem in that it is not easy for EGF to pass through the skin barrier that form a protective film having overlapped layers of keratin and keratinocytes nor to move to the skin basal layer.

Therefore, in the present invention, there is a need for research and development of a naturally-derived small molecular substance which has a similar function to EGF, is stable and small in size, and thus can easily pass through the skin barrier.

In addition, hair loss (alopecia) refers to a condition in which hair is deficient in areas where hair should normally be present, and is known to be caused by a complex association of congenital and acquired factors such as an irregular lifestyle and stress, male hormones, heredity and nutritional imbalances. As hair loss progresses, hair becomes thin and loses its strength due to the vellus hair, the anagen phase is shortened to result in hair shedding during the telogen or catagen phase, and the atrophy of the hair follicles makes it impossible to supply nutrients to the hair follicles, thereby showing a phenomenon such as loss of the function of the hair follicles.

Since hair loss may cause skin cosmetic problems in addition to medical problems, components capable of preventing hair loss or promoting hair growth have been developed as drugs, cosmetics, and the like.

Currently, representative components used to prevent hair loss or promote hair growth include minoxidil applied to the skin, finasteride administered orally, and the like, and these components are approved by the US FDA as hair loss treatment drugs and have been widely used as drugs for hair loss treatment. However, minoxidil and finasteride have side effects such as depression and sexual dysfunction, should be taken for a long period of time, and side effects, in which hair loss begins again when treatment is interrupted, toxicity and the like have been reported. For this reason, there is increasing interest in hair loss inhibitors or hair growth agents which utilize natural product-derived components that are less toxic even when administered for a long period of time, and have minimized side effects.

Piperonylic acid is a natural product-derived component isolated from various plants. Korean Patent Publication No. 10-2019-0014340 reports the results that piperonylic acid activates epidermal growth factor (EGF) receptors at the cellular level and promotes the proliferation of some skin cells. However, the above-described literature specifically describes the results of cell experiments which are only related to skin regeneration, and does not disclose any effect related to the prevention of hair loss or the promotion of hair growth.

Meanwhile, the literature [Alexandrescu, Doru T., C. Lisa Kauffman, and Constantin A. Dasanu. Dermatology Online Journal 15.3 (2009).], and the like report that an EGF receptor inhibitor exhibits a hair growth effect such as early maturation (terminal differentiation) of eyelashes and scalp hair. The above-described document is a document related to the hair loss prevention or hair growth promotion effect of an EGF receptor inhibitor, which is opposite of EGF receptor activation, and does not disclose piperonylic acid at all.

Thus, the present inventors have made intensive studies to develop a hair loss prevention agent or hair growth agent that can be administered for a long period of time and has few side effects, and surprisingly confirmed that piperonylic acid exhibits an effect of preventing hair loss or promoting hair growth clinically as well as hair cells, thereby completing the present invention.

DISCLOSURE

Technical Problem

The present inventors experimentally confirmed that a naturally-derived small molecular substance, piperonylic acid, has a similar function to epidermal growth factor (EGF), is stable and small in size, and thus can easily pass through the skin barrier, thereby completing the present invention.

Thus, an object of the present invention is to provide a pharmaceutical composition, a health functional food composition, and a cosmetic composition comprising piperonylic acid as an effective ingredient for anti-aging(delaying senescence) or regenerating the skin.

Another object of the present invention is to provide a use of piperonylic acid for preventing hair loss or promoting hair growth.

Another object of the present invention is to provide a cosmetic, pharmaceutical or food composition for preventing hair loss or promoting hair growth, comprising piperonylic acid.

However, a technical problem to be achieved by the present invention is not limited to the aforementioned problem, and other problems that are not mentioned may be clearly understood by a person with ordinary skill in the art to which the present invention pertains from the following description.

Technical Solution

To achieve the object, the present invention provides a pharmaceutical composition, a health functional food composition, and a cosmetic composition comprising piperonylic acid as an effective ingredient for anti-aging or regenerating the skin.

As an embodiment of the present invention, the composition may alleviate or treat burn wounds.

As another embodiment of the present invention, the composition may promote the proliferation or growth of cells by binding to an epidermal growth factor receptor (EGFR).

As still another embodiment of the present invention, the cells may be keratinocytes.

As yet another embodiment of the present invention, the composition may enhance resistance to cell damage due to external stimuli.

As yet another embodiment of the present invention, the external stimuli may be ultraviolet rays.

As yet another embodiment of the present invention, the composition may enhance skin elasticity.

As yet another embodiment of the present invention, the composition may alleviate skin wrinkles.

Further, the present invention provides a method for anti-aging or regenerating the skin, the method comprising administering piperonylic acid to an individual.

In addition, the present invention provides a use of piperonylic acid for producing a medicine used to delay skin senescence and regenerate the skin.

Furthermore, the present invention provides a method for alleviating or treating skin wounds, the method comprising administering piperonylic acid to an individual.

Further, the present invention provides a use of piperonylic acid for producing a medicine used to alleviate or treat skin wounds.

As an embodiment of the present invention, the skin wounds may be burns.

Further, the present inventors specifically confirmed that piperonylic acid exhibits an effect of preventing hair loss or promoting hair growth in hair cells and in humans, thereby completing the present invention.

In an aspect, the present invention provides a cosmetic composition for preventing hair loss or promoting hair growth, comprising piperonylic acid. The piperonylic acid may be derived from natural products or chemically synthesized.

The cosmetic composition may have one or more hair health improvement uses selected from the group consisting of an increase in hair thickness, an improvement in hair elasticity, an improvement in hair volume, and an increase in hair count. Specifically, the cosmetic composition may alleviate androgenic alopecia symptoms and promote the proliferation of dermal papilla cells.

The cosmetic composition of the present invention may include piperonylic acid in an amount of 0.005 wt % to 5 wt % based on the composition. The cosmetic composition may comprise one or more cosmetically acceptable additives or carriers. More specifically, the cosmetic composition may be one or more formulations selected from the group consisting of hair tonic, hair conditioner, hair essence, hair lotion, hair nourishing lotion, hair shampoo, hair rinse, hair treatment, hair cream, hair nourishing cream, hair moisturizing cream, hair massage cream, hair wax, hair aerosol, hair pack, hair nourishing pack, hair soap, hair cleansing foam, hair oil, hair drying agent, hair preservation treatment agent, hair colorant, hair waving preparation, hair decolorant, hair gel, hair glaze, hair dressing agent, hair lacquer, hair moisturizer, hair mousse and hair spray.

In another aspect, the present invention provides a pharmaceutical composition for preventing hair loss or promoting hair growth, comprising piperonylic acid. In an exemplary embodiment, the pharmaceutical composition may be one or more external skin applications selected from the group consisting of an aerosol, an ointment, a liquid, a lotion, a patch, an application powder, an oil, a cream and a gel.

In still another aspect, the present invention provides a food composition for preventing hair loss or promoting hair growth, comprising piperonylic acid.

Advantageous Effects

Piperonylic acid can be extracted from various plant species, and a composition according to the present invention has the advantage of having no side effect using the same.

Further, piperonylic acid of the present invention activates signals associated with cell survival, growth, and proliferation to exhibit the effect of increasing the resistance and survival of skin cells against external stimuli and enhancing the regeneration of the skin damaged due to external stimuli or senescence by binding to EFGR like EGF.

In addition, piperonylic acid of the present invention has a similar function to EGF, but is stable and small in size in contrast to EGF. Thus, piperonylic acid of the present invention has the advantage of being able to easily move to the skin basal layer through the skin barrier and perform its function.

Therefore, piperonylic acid of the present invention can be used in applications in various fields including medicines, quasi-drugs, cosmetics, cosmetic applications(including perfume), functional biomaterials, and functional food materials.

In addition, since the composition for preventing hair loss or promoting hair growth of piperonylic acid according to the present invention is safe and has few side effects by using a natural product-derived ingredient as an active ingredient, and has an excellent effect of alleviating androgenic alopecia symptoms and an excellent hair cell growth and proliferation effect, the composition can be usefully used in cosmetics, drugs, quasi-drugs, foods, and the like for preventing hair loss or promoting hair growth.

DESCRIPTION OF DRAWINGS

FIG. 3B is a view illustrating the top 10 EGFR binding sites of piperonylic acid predicted by the PatchDock program.

BEST MODES OF THE INVENTION

Figure 1A:
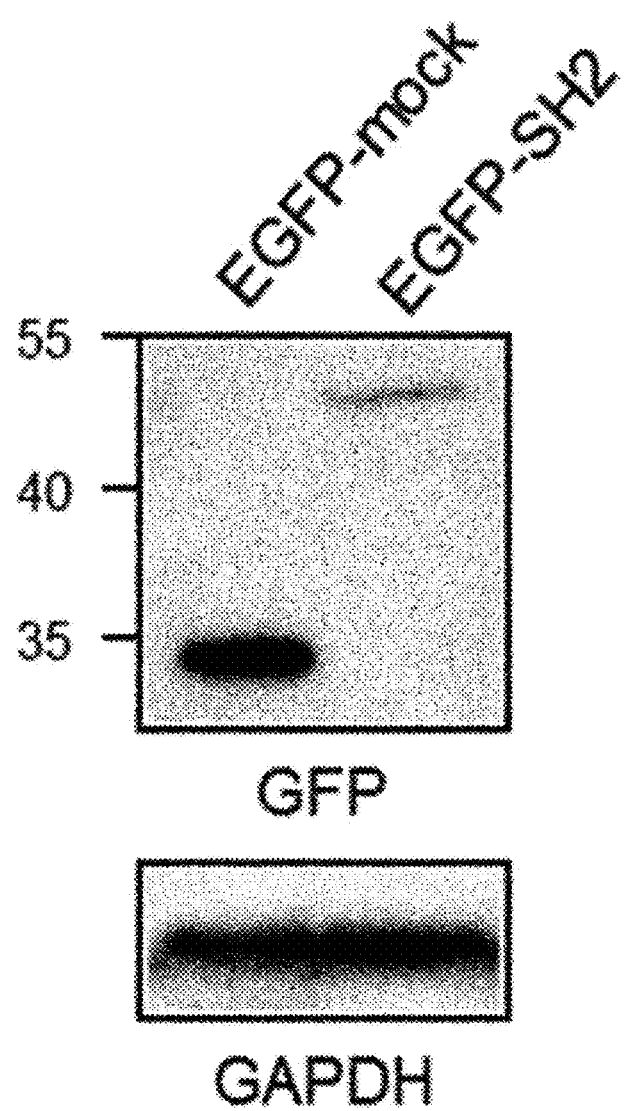
FIG. 1A is a view confirming the expression of a biosensor protein (EGFP-SH2) by intracellular injection of the EGFR activity measuring biosensor system.

Since the present invention may be modified into various forms and include various exemplary embodiments, specific exemplary embodiments will be illustrated in the drawings and described in detail in the Detailed Description. However, the description is not intended to limit the present invention to the specific exemplary embodiments, and it is to be understood that all the changes, equivalents, and substitutions belonging to the spirit and technical scope of the present invention are included in the present invention. When it is determined that the detailed description of the related publicly known art in describing the present invention may obscure the gist of the present invention, the detailed description thereof will be omitted.

The present inventors experimentally confirmed that a naturally-derived small molecular substance, piperonylic acid, has a similar function to an epidermal growth factor (EGF), is stable and small in size, and thus can easily pass through the skin barrier, thereby completing the present invention.

Accordingly, the present invention provides a pharmaceutical composition comprising piperonylic acid as an effective ingredient for anti-aging or regenerating the skin. In the present invention, piperonylic acid may be represented by the following Chemical Formula 1, and the pharmaceutical composition may include piperonylic acid or a pharmaceutically acceptable salt thereof as an effective ingredient.

[Chemical Formula 1]

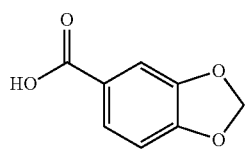

The piperonylic acid may be obtained from an extract of various plant species, and may increase the resistance and survival of skin cells against external stimuli and enhance the regeneration of the skin damaged due to external stimuli or senescence by performing a similar function to epidermal growth factor (EGF) which activates signals associated with cell survival, growth, and proliferation in the cells.

In the present specification, anti-aging means prevention or suppression of skin senescence. The skin senescence includes endogenous senescence due to the passage of time and exogenous senescence due to the external environment. The skin senescence may include skin wrinkles, blemishes, freckles, and the like. The skin wrinkles may be fine wrinkles resulting from the deterioration of the skin, and the skin wrinkles may be caused by photoaging, age, facial expression, lack of moisture, or a combination thereof. The photoaging may be skin senescence caused by exposure to ultraviolet rays (including UVA, UVB, and UVC). The alleviation of skin wrinkles may suppress or inhibit wrinkles from being produced in the skin, or may relieve wrinkles that have been already produced.

In the present specification, skin regeneration may be to prevent damage of cells from external and/or internal stimuli, alleviate wrinkles of the skin, and enhance elasticity of the skin, and includes the meaning of preventing, alleviating, or treating skin damage caused by the external environment.

In the present specification, skin damage is meant to include skin wounds such as damage or injuries occurring in the skin. The skin wounds may be selected from the group consisting of abrasions, bruises, lacerations, cut wounds, contusions, stab wounds, bed sores, burns, frostbite, skin ulcers and chemical wounds, and may be preferably burns.

Specifically, in an example of the present invention, a biosensor system was manufactured to measure the epidermal growth factor receptor (EGFR) on the cell membrane was internalized by endocytosis when the EGFR was activated. Then, it was confirmed that piperonylic acid of the present invention activated the EGFR (see Examples 1 and 2).

Therefore, according to an aspect of the present invention, the composition may bind to EGFR to promote the proliferation or growth of cells, thereby anti-aging or activating the regeneration of the skin. Cells that are proliferated or grown by the composition of the present invention may be epidermal cells, and may preferably be keratinocytes which are keratin-producing cells, but are not limited thereto.

Keratin is a protein that is a major constituent in various tissues of animals, and makes hair glossy and elastic, and imparts vitality and elasticity to the skin. Further, the keratin proteins in the keratin layer of the skin have strong resistance to chemicals, and thus may perform protective functions against chemical irritation on the skin.

In addition, as an aspect of the present invention, the present invention provides a composition comprising piperonylic acid or a pharmaceutically acceptable salt thereof for alleviating or treating burn wounds.

Specifically, in an example of the present invention, it was confirmed that piperonylic acid had cell proliferation and growth promotion efficacy through a wound healing assay which is a method for measuring the proliferation and growth of cells by culturing cells fully on a well plate, scratching a predetermined area of cells to form a wound area, and then observing the degree to which the area was filled again (see Example 8).

Therefore, according to an aspect of the present invention, the composition may delay senescence or activate the regeneration of the skin by enhancing resistance to cell damage due to external stimuli, and the external stimuli may be chemical stimuli due to cosmetics or other external preparations, physical stimuli, or ultraviolet rays, and may be preferably ultraviolet rays, but are not limited thereto.

Specifically, in an example of the present invention, in order to confirm effects of piperonylic acid of the present invention on enhancing resistance to cell damage due to ultraviolet rays (UVB), cell viability was confirmed by irradiating keratinocytes which had been treated with piperonylic acid with UVB. As a result, it was confirmed that piperonylic acid improved cell viability at a statistically significant value (see Example 9).

The pharmaceutical composition of the present invention may further include an appropriate carrier, an appropriate excipient, and an appropriate diluent, which are typically used to prepare a pharmaceutical composition. Further, the composition of the present invention may be used by being formulated in the form of an oral formulation such as a powder, a granule, a pill, a capsule, a suspension, an emulsion, a syrup, and an aerosol, an external preparation, a suppository, and a sterile injection solution, according to a typical method.

The pharmaceutical composition including piperonylic acid or a pharmaceutically acceptable salt thereof may be used by being formulated in the form of an external preparation such as a powder, a granule, a pill, a capsule, a suspension, an emulsion, a syrup, and an aerosol, and a sterile injection solution according to a typical method, and preferably may have a formulation of a cream, a gel, a patch, a spray, an ointment, a plaster, a lotion, a liniment, a paste, or a cataplasma. Examples of a carrier, an excipient or a diluent which may be included in the composition including piperonylic acid include lactose, dextrose, sucrose, an oligosaccharide, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. When the composition is prepared, the composition is prepared by using a diluent or excipient, such as a filler, an extender, a binder, a wetting agent, a disintegrant, and a surfactant, commonly used. A solid formulation for oral administration includes a tablet, a pill, a powder, a granule, a capsule, and the like, and the solid formulation is prepared by mixing at least one excipient, for example, starch, calcium carbonate, sucrose or lactose, gelatin, and the like with the extract. Further, in addition to a simple excipient, lubricants such as magnesium stearate and talc are also used. A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, an aromatic, a preservative, and the like. Examples of a formulation for parenteral administration include an aqueous sterile solution, a non-aqueous solvent, a suspension, an emulsion, a freeze-dried preparation, and a suppository. As the non-aqueous solvent and the suspension, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerogelatin, and the like.

The pharmaceutical composition according to the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including the patient's condition, body weight, sex, age, and health status, type of disease of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by a person with ordinary skill in the art to which the present invention pertains.

The pharmaceutical composition of the present invention may be administered to an individual via various routes. All modes of administration may be expected, and the pharmaceutical composition of the present invention may be administered, for example, by subcutaneous, intravenous, intramuscular, intra-uterine dural, or intracerebral injection. The pharmaceutical composition of the present invention is determined by the type of drug that is an active ingredient, as well as various related factors such as the disease to be treated, the route of administration, the age, sex, and body weight of a patient, and the severity of the disease.

As another aspect of the present invention, the present invention provides a method for anti-aging or regenerating the skin, the method including administering a pharmaceutically effective amount of the pharmaceutical composition to an individual.

As still another aspect of the present invention, the present invention provides a method for alleviating or treating burn wounds, the method including administering a pharmaceutically effective amount of the pharmaceutical composition to an individual.

As used herein, the "individual" refers to a subject in need of treatment of a disease, and more specifically, refers to a mammal such as a human or a non-human primate, a mouse, a rat, a dog, a cat, a horse, and a cow.

Further, the present invention provides a use of a composition comprising piperonylic acid or a pharmaceutically acceptable salt thereof as an effective ingredient for anti-aging or regenerating the skin.

As yet another aspect of the present invention, the present invention provides a health functional food composition comprising piperonylic acid as an effective ingredient for anti-aging or regenerating the skin. Further, piperonylic acid may be added to food for the purpose of skin regeneration, such as delaying senescence, enhancing skin elasticity or alleviating skin wrinkles. When piperonylic acid of the present invention is used as a food additive, the piperonylic acid may be added as it is or used with another food or other food ingredients, and may be appropriately used according to a typical method. The amount of effective ingredient mixed may be suitably determined according to the purpose of use (prevention, health or therapeutic treatment). In general, when a food or beverage is prepared, piperonylic acid of the present invention is added in an amount of 15 wt % or less, preferably 10 wt % or less based on the raw materials. However, in the case of long-term intake for the purpose of health and hygiene, or for the purpose of controlling health, the amount may be equal to or less than the above range, and the effective ingredient may be used in an amount equal to or more than the above range due to no problem in terms of safety.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrates is generally about 0.01 to 0.20 g, and preferably about 0.04 to 0.10 g per 100 ml of the composition of the present invention.

In addition to the aforementioned ingredients, the composition of the present invention may contain various nutrients, vitamins, electrolytes, flavors, colorants, pectic acid and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

Furthermore, the piperonylic acid exhibits the effect of promoting the growth, proliferation, and survival of cells, and thus may be provided in the form of a cosmetic composition for the purpose of skin regeneration, such as anti-aging, enhancing skin elasticity or alleviating skin wrinkles. A formulation of the cosmetic composition according to the present invention may be in the form of a skin lotion, skin softener, skin toner, astringent, lotion, milk lotion, moisturizing lotion, nourishing lotion, massage cream, nourishing cream, moisturizing cream, hand cream, foundation, essence, nourishing essence, pack, soap, cleansing foam, cleansing lotion, cleansing cream, body lotion or body cleanser.

The cosmetic composition of the present invention may further include a composition selected from the group consisting of water-soluble vitamins, oil-soluble vitamins, polymer peptides, polymeric polysaccharides, and sphingolipids.

Any water-soluble vitamin may be used as long as it can be incorporated into cosmetics, but preferred examples thereof include vitamin B1, vitamin B2, vitamin B6, pyridoxine, pyridoxine hydrochloride, vitamin B12, pantothenic acid, nicotinic acid, nicotinamide, folic acid, vitamin C, vitamin H, and the like, and salts thereof (thiamine hydrochloride, sodium ascorbate, and the like) or derivatives thereof (ascorbic acid-2-phosphate sodium salt, ascorbic acid-2-phosphate magnesium salt, and the like) are also included in the water-soluble vitamins which may be used in the present invention. The water-soluble vitamin may be obtained by a typical method such as a microbial transformation method, purification from a culture of a microorganism, an enzymatic method or a chemical synthesis method.

Any oil-soluble vitamin may be used as long as it can be incorporated into cosmetics, but preferred examples thereof include vitamin A, carotene, vitamin D2, vitamin D3, vitamin E (d1-alpha tocopherol, d-alpha tocopherol, and d-alpha tocopherol), and the like, and derivatives thereof (ascorbic palmitate, ascorbic stearate, ascorbic acid dipalmitate, d1-alpha tocopherol acetate, dl-alpha tocopherol vitamin E acetate, DL-pantothenyl alcohol, D-pantothenyl alcohol, pantothenyl ethyl ether, and the like) and the like are also included in the oil-soluble vitamins which are used in the present invention. The oil-soluble vitamin may be obtained by a typical method such as a microbial transformation method, purification from a culture of a microorganism, an enzymatic method or a chemical synthesis method.

Any polymer peptide may be used as long as it can be incorporated into cosmetics, but preferred examples thereof include collagen, hydrolyzed collagen, gelatin, elastin, hydrolyzed elastin, keratin and the like. The polymer peptide may be purified and obtained by a typical method such as purification from a culture solution of a microorganism, an enzymatic method or a chemical synthesis method, or typically may be purified from natural products such as the dermis of pigs, cows, and the like and silk fibers of silkworms and used.

Any polymeric polysaccharide may be used as long as it can be incorporated into cosmetics, but preferred examples thereof include hydroxyethyl cellulose, xanthan gum, sodium hyaluronate, chondroitin sulfate, salts thereof (sodium salts, and the like), or the like. For example, chondroitin sulfate, salts thereof, or the like may be typically purified from mammals or fish and used.

Any sphingolipid may be used as long as it can be incorporated into cosmetics, but preferred examples thereof include ceramide, phytosphingosine, glycosphingolipid and the like. The sphingolipids may be typically purified from mammals, fish, shellfish, yeast, plants, or the like by a typical method, or may be obtained by a chemical synthesis method.

Other ingredients typically incorporated into cosmetics may also be blended with the cosmetic composition of the present invention, if necessary, together with the essential ingredients.

Examples of other blended ingredients which may be added include oil and fat ingredients, a moisturizer, an emollient, a surfactant, organic and inorganic pigments, an organic powder, an ultraviolet absorbent, a preservative, a bactericide, an antioxidant, a plant extract, a pH adjuster, an alcohol, a colorant, a fragrance, a circulation accelerator, a cooling agent, an antiperspirant, purified water, and the like.

Examples of the oil and fat ingredients include ester-based oils and fats, hydrocarbon-based oils and fats, silicone-based oils and fats, fluorine-based oils and fats, animal oils and fats, plant oils and fats, and the like.

Examples of the ester-based oils and fats include ester-based oils and fats such as glyceryl tri 2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoalkyl neopentanoate, tri(capryl, capric acid)glyceryl, tri 2-ethylhexanoic acid trimethylol propane, triisostearic acid trimethyol propane, tetra 2-ethylhexanoic acid pentaerythritol, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, 2-ethylhexanoic acid cetostearyl, 2-ethylhexanoic acid stearyl, hexyl isostearate, ethylene glycol dioctanoate, ethylene glycol dioleate, propylene glycol dicaprylate, di(capryl, capric acid)propylene glycol, propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononate, hexyldecyl neodecanoate, octyldodecyl neodecanoate, isocetyl isostearate, isostearyl isostearate, octyldecyl isostearate, polyglycerin ester oleate, polyglycerin ester isostearate, isocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stealoyl hydroxystearate, stearyl 12-stealoyl hydroxystearate, isostearyl 12-stealoyl hydroxystearate, or the like.

Examples of the hydrocarbon-based oils and fats include hydrocarbon-based oils and fats such as squalene, liquid paraffin, alpha-olefin oligomers, isoparaffin, sericin, paraffin, liquid isoparaffin, polybutene, microcrystalline wax, and Vaseline, or the like.

Examples of the silicone-based oils and fats include polymethyl silicone, methylphenyl silicone, methylcyclopolysiloxane, octamethyl polysiloxane, decamethyl polysiloxane, dodecamethyl cyclosiloxane, a dimethylsiloxane methyl cetyloxysiloxane copolymer, a dimethylsiloxane methyl stearoxysiloxane copolymer, alkyl-modified silicone oil, amino-modified silicone oil, and the like.

Examples of the fluorine-based oils and fats include perfluoropolyether, and the like.

Examples of the animal or plant oils and fats include animal or plant oils and fats such as avocado oil, almond oil, olive oil, sesame oil, rice bran oil, new flower oil, soybean oil, corn oil, rapeseed oil, apricot kernel oil, palm kernel oil, palm oil, castor oil, sunflower oil, grapeseed oil, cottonseed oil, palm oil, kukui nut oil, wheat germ oil, rice germ oil, shea butter, evening primrose oil, macadamia nut oil, meadow home oil, egg yolk oil, beef tallow, horse oil, mink oil, orange roughy oil, jojoba oil, candelilla wax, carnauba wax, liquid lanolin and hardened castor oil.

Examples of the moisturizer include a water-soluble low molecular moisturizer, a fat-soluble low molecular moisturizer, a water-soluble polymer, a fat-soluble polymer, and the like.

Examples of the water-soluble low molecular moisturizer include serine, glutamine, sorbitol, mannitol, pyrrolidone-sodium carboxylate, glycerin, propylene glycol, 1,3-butylene glycol, ethylene glycol, polyethylene glycol B (polymerization degree n=2 or more), polypropylene glycol (polymerization degree n=2 or more), polyglycerin B (polymerization degree n=2 or more), lactic acid, lactate, and the like.

Examples of the fat-soluble low molecular moisturizer include cholesterol, cholesterol ester, and the like.

Examples of the water-soluble polymer include a carboxyvinyl polymer, polyaspartate, tragacanth, xanthane gum, methyl cellulose, hydroxymethyl cellulose, hydroxyethyl cellulose, hydroxypropyl cellulose, carboxymethyl cellulose, water-soluble chitin, chitosan, dextrin, and the like.

Examples of the fat-soluble polymer include a polyvinylpyrrolidone•eicosene copolymer, a polyvinylpyrrolidone•hexadecene copolymer, nitrocellulose, dextrin fatty acid ester, high molecular silicone, and the like.

Examples of the emollient include long-chain acylglutamate cholesteryl ester, cholesteryl hydroxystearate, 12-hydroxystearic acid, stearic acid, rosin acid, lanolin fatty acid cholesteryl ester, and the like.

Examples of the surfactant include a nonionic surfactant, an anionic surfactant, a cationic surfactant, an amphoteric surfactant, and the like.

Examples of the nonionic surfactant include auto-emulsified glycerin monostearate, propylene glycol fatty acid ester, glycerin fatty acid ester, polyglycerin fatty acid ester, sorbitan fatty acid ester, polyoxyethylene (POE) sorbitan fatty acid ester, POE sorbitol fatty acid ester, POE glycerin fatty acid ester, POE alkyl ether, POE fatty acid ester, POE hardened castor oil, POE castor oil, a polyoxyethylene polyoxypropylene (POE•POP) copolymer, POE•POP alkyl ether, polyether-denatured silicone, alkanolamide laurate, alkylamine oxide, hydrogenated soybean phospholipid, and the like.

Examples of the anionic surfactant include fatty acid soap, α-acylsulfonate, alkyl sulfonates, alkyl allyl sulfonates, alkyl naphthalene sulfonates, alkyl sulfates, POE alkyl ether sulfate, alkylamide sulfates, alkyl phosphates, POE alkyl phosphates, alkylamide phosphates, alkyloyl alkyl taurine salts, N-acylamino acid salts, POE alkyl ether carboxylates, alkylsulfosuccinates, sodium alkylsulfoacetates, acylated hydrolyzed collagen peptide salts, perfluoroalkyl ester phosphate, and the like.

Examples of the cationic surfactant include alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, diethylaminoethylamide stearate, dimethylaminopropylamide stearate, lanolin derivative quaternary ammonium salts, and the like.

Examples of the amphoteric surfactant include amphoteric surfactants of the following types: carboxybetaines, amidebetaines, sulfobetaines, hydroxysulfobetaines, amidesulfobetaines, phosphobetaines, aminocarboxylates, imidazoline derivatives and amideamines.

Examples of the organic and inorganic pigments include inorganic pigments such as silicic acid, anhydrous silicic acid, magnesium silicate, talc, sericite, mica, kaolin, bengala, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine blue, chromium oxide, chromium hydroxide, carmine, and complexes thereof; organic pigments such as polyamide, polyester, polypropylene, polystyrene, polyurethane, vinyl resins, urea resins, phenol resins, fluororesins, silicone resins, acrylic resins, melamine resins, epoxy resins, polycarbonate resins, divinyl a benzene•styrene copolymer, silk powder, cellulose, CI pigment yellow and CI pigment orange; complex pigments of these inorganic pigments and organic pigments, and the like.

Examples of the organic powder include metal soaps such as calcium stearate; alkylphosphoric acid metal salts such as sodium zinc cetylphosphate, zinc laurylphosphate and calcium laurylphosphate; acylamino acid polyvalent metal salts such as N-lauroyl-β-alanine calcium, N-lauroyl-β-alanine zinc and N-lauroylglycine calcium; amidesulfonic acid polyvalent metal salts such as N-lauroyl-taurine calcium and N-palmitoyl-taurine calcium; N-acyl basic amino acids such as N-ε-lauroyl-L-lysine, N-ε-palmitoyllysine, N-α-palmitoylornithine, N-α-lauroylarginine and N-α-hardened beef tallow fatty acid acylarginine; N-acylpolypeptides such as N-lauroylglycylglycine; α-amino fatty acids such as α-aminocaprylic acid and α-aminolauric acid; polyethylene, polypropylene, nylon, polymethyl methacrylate, polystyrene, a divinyl benzene•styrene copolymer, ethylene tetrafluoride, and the like.

Examples of the ultraviolet absorbent include para-aminobenzoic acid, ethyl para-aminobenzoate, amyl para-aminobenzoate, octyl para-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl para-methoxycinnamate, octyl para-methoxycinnamate, glyceryl mono(2-ethylhexanoate) dipara-methoxycinnamate, isopropyl para-methoxycinnamate, diisopropyl•diisopropylcinnamic acid ester mixtures, urocanic acid, ethyl urocanate, hydroxymethoxybenzophenone, hydroxymethoxybenzophenonesulfonic acid and salts thereof, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, and the like.

Examples of the bactericide include hinokitiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, photosensitizing dye No. 301, sodium mononitroguaiacol, undecylenic acid, and the like.

Examples of the antioxidant include butylhydroxyanisole, propyl gallate, erythorbic acid, and the like.

Examples of the pH adjuster include citric acid, sodium citrate, malic acid, sodium malate, fumaric acid, sodium fumarate, succinic acid, sodium succinate, sodium hydroxide, disodium hydrogen phosphate, and the like.

Examples of the alcohol include higher alcohols such as cetyl alcohol.

Further, the blended ingredients that may be added in addition to the aforementioned ingredients are not limited thereto, and any of the ingredients can be blended within a range that does not impair the purpose and effect of the present invention, but is blended at preferably 0.01 to 5 wt %, and more preferably 0.01 to 3 wt % based on the total weight.

When the formulation of the present invention is a lotion, a paste, a cream, or a gel, an animal fiber, a vegetable fiber, a wax, paraffin, starch, tragacanth, a cellulose derivative, polyethylene glycol, silicone, bentonite, silica, talc, zinc oxide, or the like may be used as the carrier ingredient.

When the formulation of the present invention is a powder or a spray, lactose, talc, silica, aluminum hydroxide, calcium silicate, or a polyamide powder may be used as the carrier ingredient, and in particular, when the formulation is a spray, the formulation may include a propellent such as chlorofluorohydrocarbon, propane/butane or dimethyl ether.

When the formulation of the present invention is a solution or an emulsion, a solvent, a solubilizer or an emulsifier is used as the carrier ingredient, and examples thereof include water, ethanol, isopropanol, ethyl carbonate, ethyl acetate, benzyl alcohol, benzyl benzoate, propylene glycol, 1,3-butylglycol oil, glycerol aliphatic esters, polyethylene glycol or fatty acid esters of sorbitan.

When the formulation of the present invention is a suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used as the carrier ingredient.

When the formulation of the present invention is a surfactant-containing cleanser, an aliphatic alcohol sulfate, an aliphatic alcohol ether sulfate, sulphosuccinic acid monoester, isethionate, an imidazolinium derivative, methyltaurate, sarcosinate, fatty acid amide ether sulfate, alkylamidobetain, an aliphatic alcohol, fatty acid glyceride, fatty acid diethanolamide, a vegetable oil, a lanolin derivative, an ethoxylated glycerol fatty acid ester, or the like may be used as the carrier ingredient.

In addition, the present invention provides a cosmetic composition, pharmaceutical composition and food composition for preventing hair loss or promoting hair growth, comprising piperonylic acid, and the description thereof will be described below in detail.

In an aspect, the present invention provides a cosmetic composition for preventing hair loss or promoting hair growth, comprising piperonylic acid. Here, piperonylic acid is a compound represented by the above Chemical Formula 1.

In the present invention, piperonylic acid may be derived from natural products. For example, the piperonylic acid of the present invention may be included in or isolated from a Piperaceae plant (*Piper nigrum* L. or *Piper longum* L.) extract. Alternatively, the piperonylic acid of the present invention may be chemically synthesized. The method for preparing the piperonylic acid of the present invention has been publicly known in the art, and the piperonylic acid of the present invention is readily available commercially (CAS No.: 94-53-1).

In the present invention, piperonylic acid comprises a cosmetically acceptable salt of piperonylic acid in addition to piperonylic acid in the form of a free acid.

In the present invention, piperonylic acid may be comprised as an active ingredient for preventing hair loss or promoting hair in the composition.

As used herein, the term "hair" refers to a filamentous structure consisting of keratinized epithelial cells and coming out of the surface of the skin, and includes both body hair and head hair.

As used herein, the term "hair loss" refers to a phenomenon in which hair falls out of the skin or a state in which hair becomes thin and fine, and may be used interchangeably with alopecia symptoms. In the present invention, hair loss includes dystrophic alopecia, endocrine disorder alopecia, vascular impaired alopecia, adult alopecia, alopecia gradus, alopecia areata, alopecia neurotica, alopecia pityrodes, trichotillomania, malignant alopecia, female pattern alopecia, male pattern alopecia, androgenic alopecia, telogen effluvium, tinea capitis, alopecia totalis, hypotrichosis, hereditary hypotrichosis simplex, alopecia universalis, chemotherapy-induced alopecia, mechanical alopecia, traumatic alopecia, pressure alopecia, anagen effluvium, syphilitic alopecia, alopecia seborrheica, effluvium symptomaticum, alopecia cicatrisata or alopecia congenita, but is not limited thereto. In the present invention, hair loss should be understood to include all symptoms classified as hair loss, regardless of the direct or indirect cause of the onset.

In the present invention, prevention of hair loss refers to all actions in which the occurrence or onset of one or more symptoms associated with hair loss is suppressed or delayed, and is not necessarily limited to complete suppression of the onset of hair loss.

In the present invention, promotion of hair growth refers to all phenomena that directly or indirectly contribute to hair production or growth.

Figure 11:
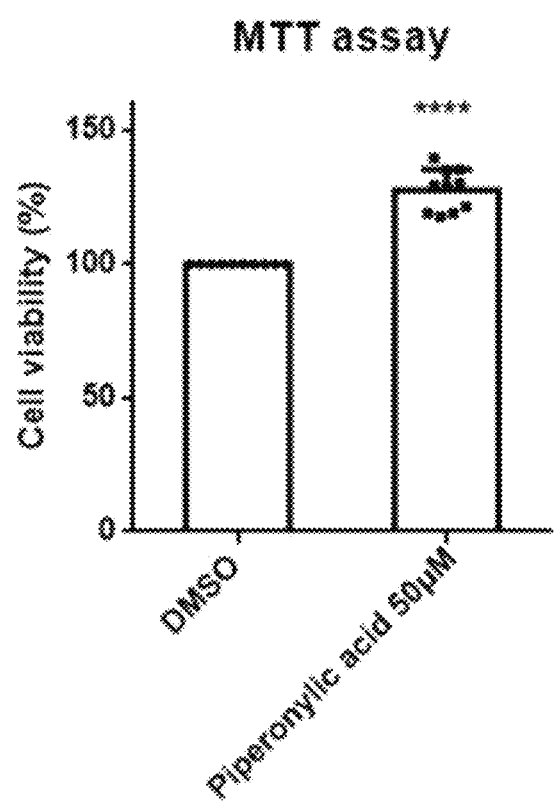
FIG. 11 illustrates the results of confirming the effect of piperonylic acid on the promotion of growth and proliferation of dermal papilla cells derived from androgenic alopecia.
Figure 12:
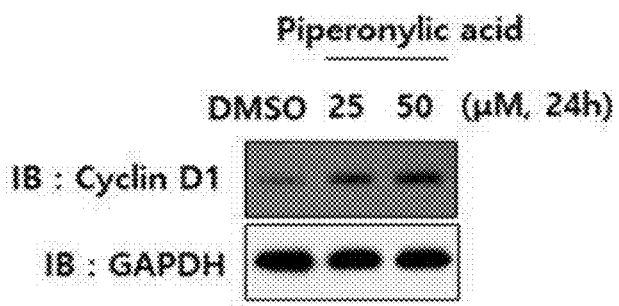
FIG. 12 illustrates the results of confirming an increase in expression of cyclin D protein involved in the promotion of growth and proliferation during treatment of dermal papilla cells derived from androgenic alopecia with piperonylic acid.
Figure 12:
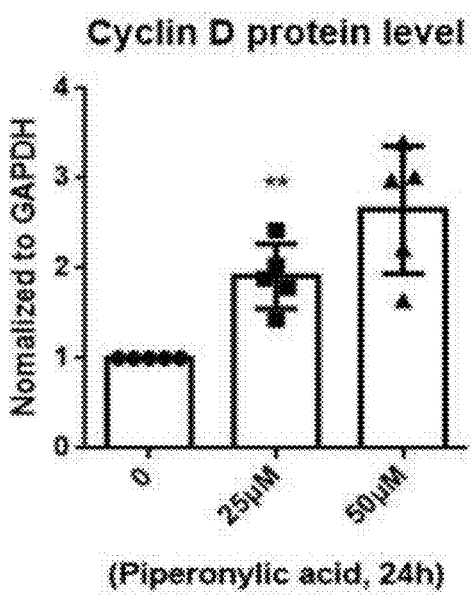
Figure 13:
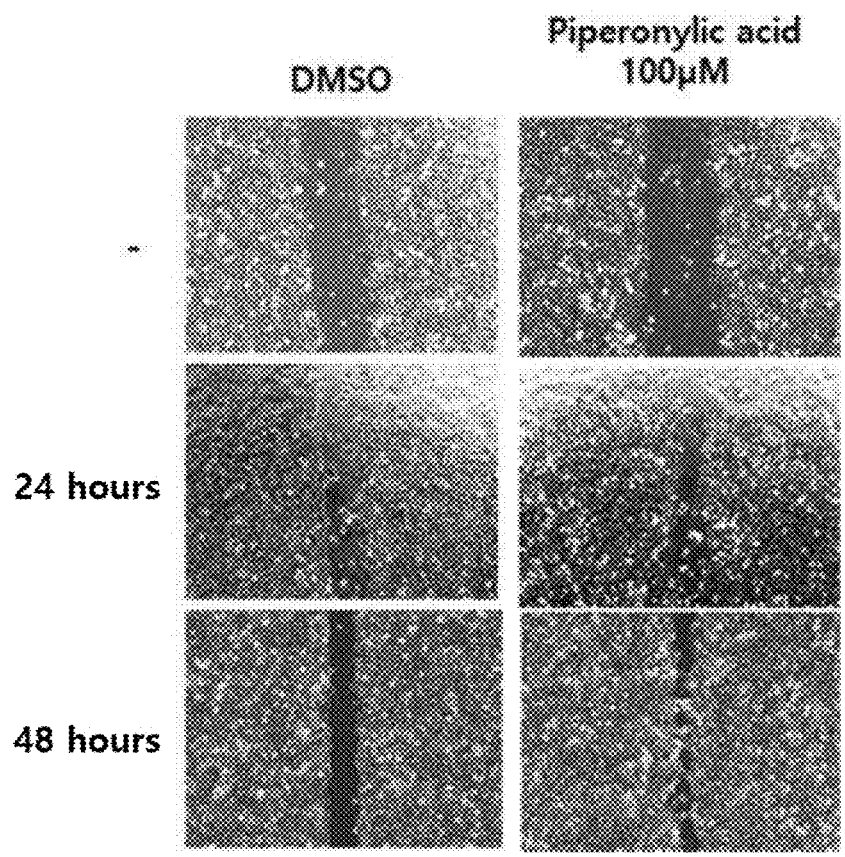
FIG. 13 is a set of photographs illustrating the results of confirming the effect of piperonylic acid on the promotion of growth and proliferation of dermal papilla cells derived from androgenic alopecia.

In the exemplary embodiments of the present invention, it was experimentally confirmed that piperonylic acid has an effect of promoting the proliferation of dermal papilla cells (FIGS. 11 to 13).

Figure 14:
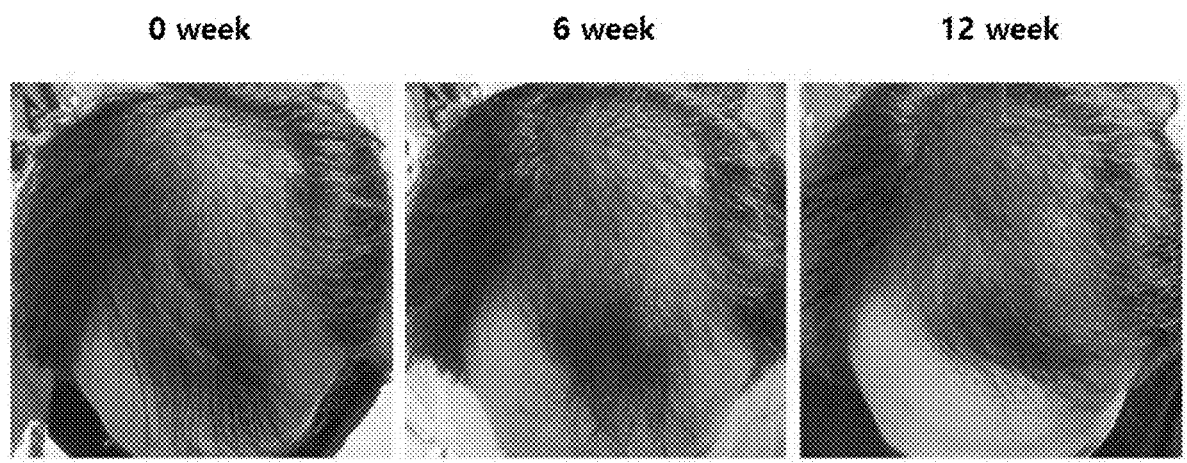
FIG. 14 is a set of photographs illustrating the results of a human body application test that confirmed the effect of piperonylic acid on the alleviation of androgenic alopecia symptoms in subjects.
Figure 15:
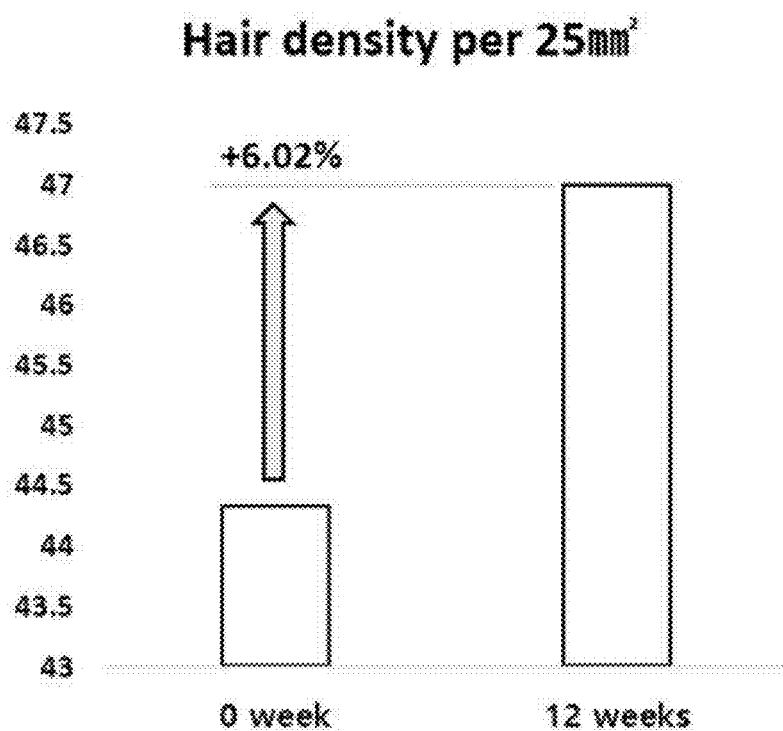
FIG. 15 is a graph illustrating the results of a human body application test that confirmed the effect of piperonylic acid on the alleviation of androgenic alopecia symptoms in subjects.

In general, various types of cells such as dermal papilla cells and germinal matrix cells interact with each other in hair growth, thus, in addition to cell proliferation ability experiments targeting some hair cells, clinical hair loss prevention or hair growth promotion effects need to be confirmed. Therefore, in the present invention, it was confirmed that when the composition comprising piperonylic acid is applied to the scalp of men who experience androgenic alopecia symptoms for 6 weeks or 12 weeks or more, a hair loss prevention or hair growth promoting effect is exhibited (FIGS. 14 and 15).

Therefore, the composition comprising piperonylic acid of the present invention may be usefully utilized for preventing hair loss or promoting hair growth.

The composition of the present invention has a hair health improvement effect, and specifically, may exhibit one or more hair health improvement effects selected from the group consisting of an increase in hair thickness, an improvement in hair elasticity, an improvement in hair volume, and an increase in hair count.

The compositions of the present invention may alleviate androgenic alopecia symptoms. In the present invention, the term "androgenic alopecia" is defined in the same sense as used in the art. Androgenic alopecia is alopecia caused by a genetic predisposition and the action of a male hormone androgen. When testosterone reaches the hair follicles, it is converted into dihydrotestosterone (DHT) by 5α-reductase, and DHT is known to make the hair follicles atrophy and gradually thin the hair to show alopecia symptoms. Androgenic alopecia symptoms may appear in both male pattern alopecia and female pattern alopecia.

The cosmetic composition of the present invention may promote the proliferation of dermal papilla cells. Specifically, the dermal papilla cells of the present invention may be dermal papilla cells associated with androgenic alopecia symptoms. In the exemplary embodiments of the present invention, it was confirmed that the cosmetic composition of the present invention has an effect of promoting the growth and proliferation of dermal papilla cells isolated from the hair follicles of the scalp of a male patient with androgenic alopecia (FIGS. 11 to 13).

In addition, the cosmetic composition of the present invention may alleviate hair loss in patients with androgenic alopecia. Specifically, in the present invention, as a result of applying the cosmetic composition comprising piperonylic acid to subjects once a day for 12 weeks, it was confirmed that the androgenic alopecia symptoms were alleviated and the hair count and the like increased statistically (FIGS. 14 and 15).

The cosmetic composition of the present invention may exhibit an effect of preventing hair loss or promoting hair growth alone, and may further comprise one or more additional components that assist the hair loss preventing or hair growth promoting effect of piperonylic acid. For example, the cosmetic composition of the present invention may further comprise a 5α-reductase inhibitory component, a hair bulb and hair follicle cell active component, a hair follicle cell blood flow enhancing component, a bactericidal component, an anti-dandruff agent, a keratin softener, a refreshing agent, a moisturizer, and the like, but is not limited thereto. Since the technical spirit of the present invention is that piperonylic acid alone exhibits an effect of preventing hair loss or promoting hair growth, one or more additional components which may be comprised in the cosmetic composition of the present invention other than piperonylic acid may or may not be arbitrarily comprised.

The cosmetic composition comprising piperonylic acid of the present invention may be utilized as a functional cosmetic product useful for preventing or ameliorating dryness, cracking, shedding, keratinization, and the like due to functional weakening of skin or hair.

In the present invention, piperonylic acid comprised in a cosmetic composition should be used in an appropriate content that does not cause skin toxicity while exhibiting an effect of preventing hair loss or promoting hair growth when used as a cosmetic product, and the present inventors confirmed that 0.005 wt % to 5 wt % is an appropriate content based on the composition (FIGS. 14 and 15). More preferably, 0.01 wt % to 1.0 wt % of piperonylic acid based on the composition may be comprised in the composition.

The cosmetic composition for preventing hair loss or promoting hair growth of the present invention may comprise one or more cosmetically acceptable additives or carriers in addition to piperonylic acid.

In the present invention, the cosmetically acceptable additive may be used in an appropriate mixture with a cosmetic additive known in the art, for example, a filler, a binder, a disintegrant, a lubricant, a suspending agent, a solvent, an antioxidant, a pH adjuster, a wetting agent, a sweetening agent, a preservative, or the like as long as it does not impair the functionality of piperonylic acid in light of the physicochemical properties of piperonylic acid.

In the present invention, the cosmetically acceptable carrier may be used in an appropriate mixture with a cosmetic carrier known in the art, for example, a gelling agent, an activator, a preservative, an antioxidant, a stabilizer, a solubilizing agent, a vitamin, a solvent, a fragrance, a filler, a blocker, a pigment, a deodorant, a dye, or the like as long as it does not impair the functionality of piperonylic acid in light of the physicochemical properties of piperonylic acid.

In an exemplary embodiment, the cosmetic composition of the present invention may further comprise one or more additives or carriers such as a carbomer, an alcohol polyethylene ether (for example, octyldodeceth-16), butylene glycol, 1,2-hexanediol, ethanol or a combination thereof in order to improve the hair loss prevention or hair growth promoting functionality of piperonylic acid and secure the safety of the skin when applied to human skin (see Example 10).

The cosmetic composition of the present invention may be prepared in a formulation that can be appropriately applied to hair for preventing hair loss or promoting hair growth. Specifically, the cosmetic composition of the present invention may be prepared as one or more formulations selected from the group consisting of hair tonic, hair conditioner, hair essence, hair lotion, hair nourishing lotion, hair shampoo, hair rinse, hair treatment, hair cream, hair nourishing cream, hair moisturizing cream, hair massage cream, hair wax, hair aerosol, hair pack, hair nourishing pack, hair soap, hair cleansing foam, hair oil, hair drying agent, hair preservation treatment agent, hair colorant, hair waving preparation, hair decolorant, hair gel, hair glaze, hair dressing agent, hair lacquer, hair moisturizer, hair mousse and hair spray.

The cosmetic composition of the present invention may be locally administered by applying it to a skin site requiring hair loss prevention or hair growth promotion once to three times a day in an appropriate volume, and may be administered for 6 weeks or more, 12 weeks or more, or 30 weeks or more. The administration frequency and the administration cycle may be appropriately adjusted according to the severity of hair loss symptoms and the desired degree of hair promotion.

The cosmetic composition of the present invention may allow the user to apply the composition directly to the skin or may be applied to the skin by a device or instrument that allows the composition to be appropriately applied to the hair.

The cosmetic composition of the present invention may be used in combination with one or more foods, drugs or cosmetics for preventing hair loss or promoting hair growth, and may be used together with or before and after hair transplantation.

In another aspect, the present invention provides a pharmaceutical composition for preventing hair loss or promoting hair growth, comprising piperonylic acid. The pharmaceutical composition may be used as a drug or a quasi-drug.

In the present invention, the pharmaceutical composition for preventing hair loss or promoting hair growth may be in various formulations suitable for oral or parenteral administration. In the present invention, the formulations for oral administration include, for example, tablets, pills, powders, powder remedy, granules, pellets, capsules, troches, lozenges, suspensions, emulsions, syrups, elixirs and the like, but are not limited thereto. In the pharmaceutical composition of the present invention, the formulations for parenteral administration may include, for example, injections, suppositories, respiratory inhalers, aerosols, ointments, liquid, lotion, patch, coating powder, oil, cream, gel, and the like, but are not limited thereto.

In the present invention, the pharmaceutical composition may be administered orally or parenterally depending on the purpose. In the present invention, the parenteral administration includes, for example, intraperitoneal administration, rectal administration, subcutaneous administration, intravenous administration, intramuscular administration, thoracic administration, cerebrovascular administration, transdermal administration and hair administration, and includes include applying, spraying, or inhaling the composition to a diseased area, but is not limited thereto. In specific exemplary embodiments of the present invention, the pharmaceutical composition of the present invention may be applied locally.

Regarding the specific usage forms of the pharmaceutical composition of the present invention, the same as described in the above-described cosmetic composition is applied, as long as there is no contradiction In still another aspect, the present invention provides a food composition for preventing hair loss or promoting hair growth, comprising piperonylic acid. In the present invention, the food composition may be in the form of a food in a typical sense, such as a beverage, a drink, a powder, a tablet and a health functional food.

In an exemplary embodiment, the food composition of the present invention may be a health functional food. In the present invention, the "health functional food" refers to a food manufactured and processed such that a bioregulatory function can be efficiently exhibited in addition to nutritional supply by using raw materials and ingredients having functionality useful for the human body.

In yet another aspect, the present invention provides a method for promoting the growth or proliferation of hair cells by treating hair cells in vitro with piperonylic acid. The hair cells may be dermal papilla cells, and specifically, may be the dermal papilla cells of a patient with androgenic alopecia (FIGS. 11 to 13). The piperonylic acid used in the method may be used at a concentration of 10 to 1,000 μM, but the concentration is not limited thereto.

The present invention also provides a method of preventing hair loss or promoting hair growth, the method comprising administering a composition comprising an effective amount of piperonylic acid to a subject in need thereof.

The present invention also provides a medium composition for culturing hair cells, comprising piperonylic acid as an active ingredient. The hair cells may be dermal papilla cells, and specifically, may be the dermal papilla cells of a patient with androgenic alopecia, and piperonylic acid may be used at a concentration of 10 to 1,000 μM, but the concentration is not limited thereto.

Modes of the Invention

Since the present invention may be modified into various forms and include various exemplary embodiments, specific exemplary embodiments will be illustrated in the drawings and described in detail in the Detailed Description. However, the description is not intended to limit the present invention to the specific exemplary embodiments, and it is to be understood that all the changes, equivalents, and substitutions belonging to the spirit and technical scope of the present invention are included in the present invention. When it is determined that the detailed description of the related publicly known art in describing the present invention may obscure the gist of the present invention, the detailed description thereof will be omitted.

Hereinafter, preferred Examples for helping the understanding of the present invention will be suggested. However, the following Examples are provided only to more easily understand the present invention, and the contents of the present invention are not limited by the following Examples.

EXAMPLES

Example 1. Manufacture of a Biosensor System That Measures EGFR Activation

When EGFR is activated, phosphorylation occurs at the tyrosine residue of the cytoplasmic portion, and signals are transmitted while various proteins are connected to this portion. As a representative linker protein, there is Grb2, and the SH2 domain of Grb2 serves to bind to the phosphorylated tyrosine residue. When the EGFR activation continues to be maintained, EGFR follows a feedback mechanism in which it is internalized inside cells and degraded. Using these characteristics, a biosensor system was manufactured such that EGFR internalization by the EGFR activation could be measured by a fluorescent protein. Specifically, an EGFP-SH2 vector was manufactured by removing only the SH2 domain of Grb2 and inserted it in an enhanced green fluorescent protein (EGFP) vector using recombinant DNA technology, and then introduced it into A549 cells for expression.

As a result, as illustrated in FIG. 1A, it was confirmed that the manufactured EGFP-SH2 biosensor protein was expressed at the expected size.

Subsequently, it was confirmed whether the EGFR activation was measured by culturing cells in which EGFP was introduced into the biosensor system in a serum-free medium for 24 hours, and then treating the cells with EGF (100 ng/ml).

Figure 1B:
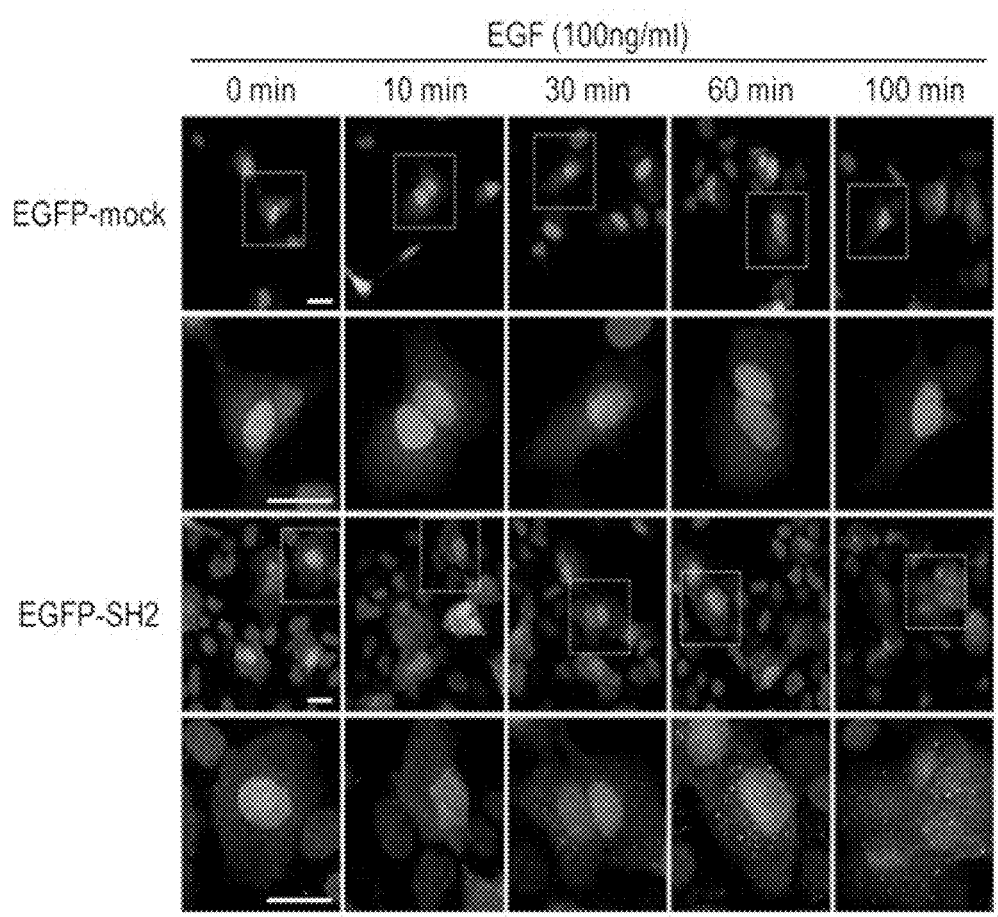
FIG. 1B is a view confirming that the biosensor system is activated by EGF.

As a result, as illustrated in FIG. 1B, it was confirmed that only in the cells introduced with the biosensor, the densely packed biosensor was appeared as fluorescence signals in the form of small dots arounds the internalized EGFR when 30 minutes after EGF treatment.

In order to confirm whether such a phenomenon was induced by other growth factors, cells were treated with FGF1, FGF2, and FGF7 which are fibroblast growth factors (FGFs) in the same manner to detect a fluorescence signal.

Figure 1C:
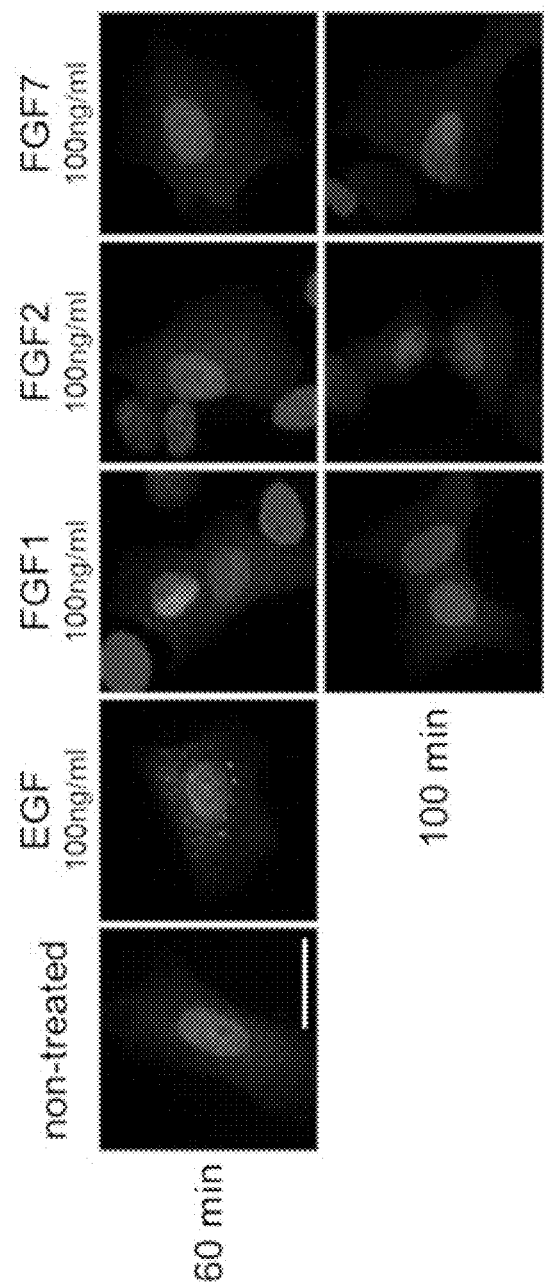
FIG. 1C is a view confirming that the biosensor system has EGF selectivity.

As a result, as illustrated in FIG. 1C, it was confirmed that no biosensor signal was shown by other growth factors. As the EGF selectivity of the manufactured biosensor system was verified, a stable cell line in which the biosensor was stably expressed was selected.

Example 2. Piperonylic Acid Inducing EGFR Activation in Biosensor System

After the biosensor system cells manufactured in Example 1 were treated with 100 μM of piperonylic acid (purchased from Sigma-Aldrich), a change in fluorescence signal was observed. After being cultured in a serum-free medium for 24 hours, the cells were treated with piperonylic acid.

Figure 2:
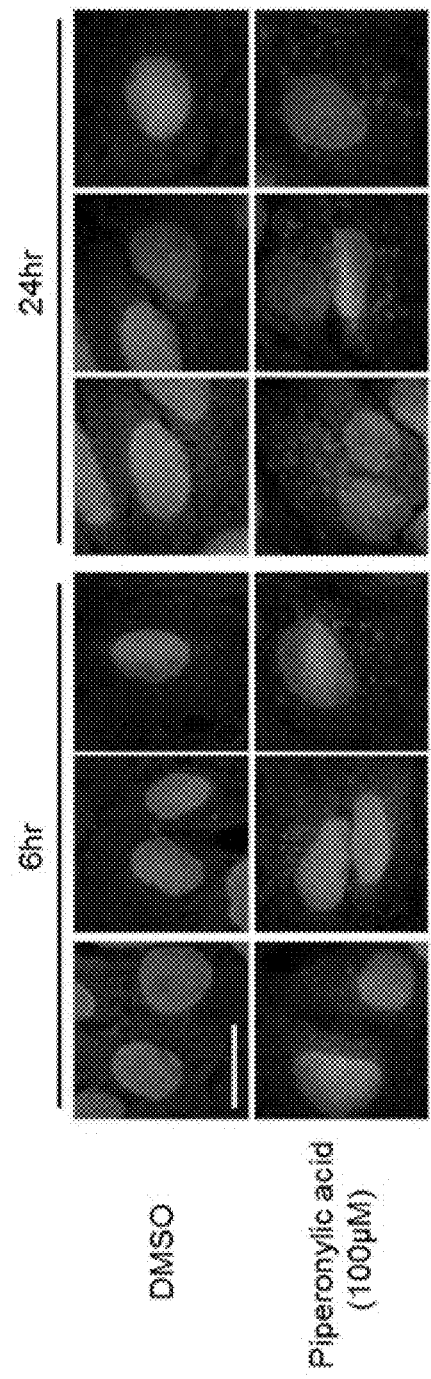
FIG. 2 is a view confirming that the biosensor system is activated by piperonylic acid.

As a result, as illustrated in FIG. 2, it could be confirmed that compared to a control which was treated with only the solvent DMSO, EGFR was activated in the cells treated with 100 μM of piperonylic acid.

Example 3. Interaction of EGFR With Piperonylic Acid

In order to investigate the mechanism of EGFR activation by piperonylic acid confirmed in Example 2, it was confirmed in the present example whether piperonylic acid could interact with EGFR. For this purpose, piperonylic acid-4B bead was manufactured by conjugating piperonylic acid to a Cyanogen bromide-activated-Sepharose 4B bead purchased from Sigma-Aldrich. Equal amounts of HaCaT cell lysates were incubated with piperonylic acid-4B bead and control-4B used as the control, and proteins bound to the bead were analyzed by the Western blotting method. An anti-EGFR antibody was used in order to measure EGFR among the precipitated proteins, and anti-Actin and anti-GAPDH antibodies against actin and GAPDH proteins present in large amounts as housekeeping genes were used in order to support that the binding to piperonylic acid was selective.

Figure 3A:
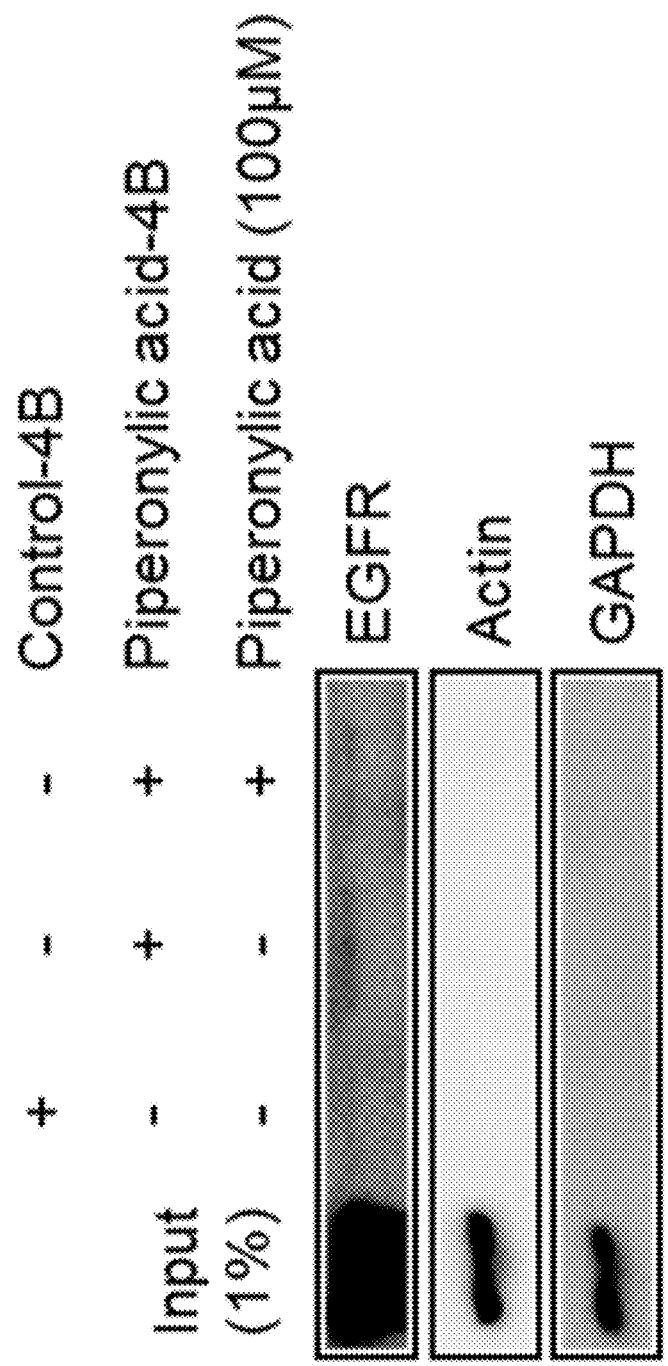
FIG. 3A is a view confirming that EGFR binds to a piperonylic acid conjugated Sepharose 4B bead.

As a result, as illustrated in FIG. 3A, it was confirmed that EGFR was bound to piperonylic acid-4B bead to which piperonylic acid was linked, and it was confirmed that when interaction with the bead was competed for by adding 100 μM of free piperonylic acid with the cell lysate, the amount of EGFR bound thereto was reduced.

In order to see where these interactions occur in EGFR, an in silico analysis was performed using the PatchDock program, which can predict the binding site.

Figure 3C:
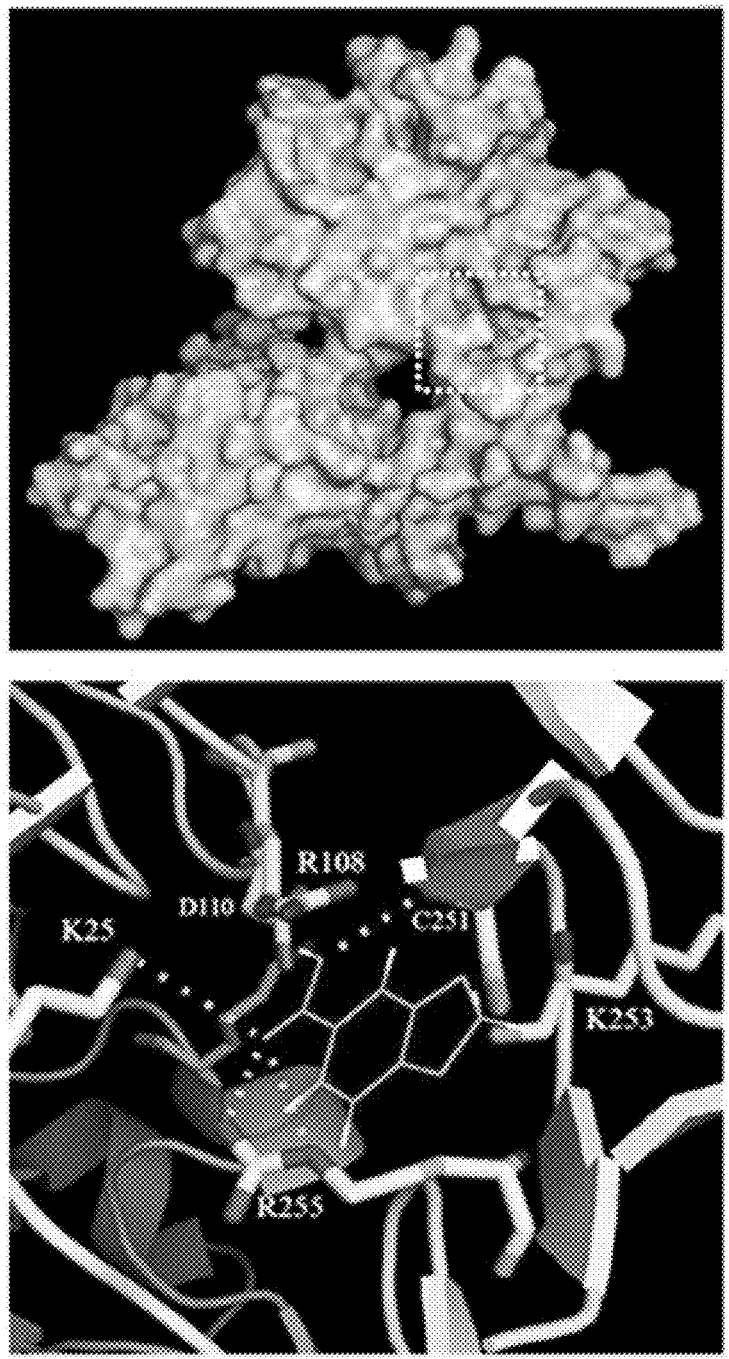
FIG. 3C illustrates the highest scoring binding site (blue) of piperonylic acid binding to EGFR. Purple indicates the binding site of EGF.

As a result, as illustrated in FIGS. 3B and 3C, a prediction was made based on the three-dimensional structural database (1MOX) of the extracellular domain of EGFR, and as a result, many positions where piperonylic acid could bind were found. In addition, as a result of analyzing the position where the highest score could be bound among the top 10 predicted scoring positions, there was a slight difference from the position where EGF binds, but if the binding of piperonylic acid induces the three-dimensional structural deformation of EGFR even incompletely, it was expected that activation would occur.

Example 4. Activation of EGFR by Piperonylic Acid

In order to confirm whether the binding of piperonylic acid with EGFR directly induces the EGFR activation, HaCaT cells cultured in a serum-free medium were treated with piperonylic acid at a concentration of 100 μM for 10 minutes, and then the activation was measured through an increasing tyrosine phosphorylation of EGFR. Specifically, after only EGFR was precipitated from 500 μg of cell lysate by immunoprecipitation using anti-EGFR antibody and protein-G agarose beads, the level of tyrosine phosphorylation was analyzed by Western blotting method.

Figure 4:
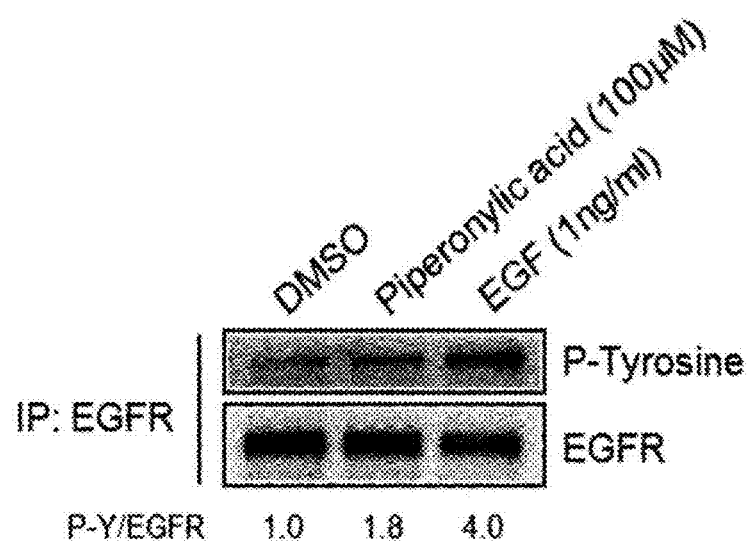
FIG. 4 is a view confirming that tyrosine phosphorylation of EGFR is increased by piperonylic acid. The tyrosine phosphorylation of EGFR means that EGFR is activated.

As a result, as illustrated in FIG. 4, the tyrosine phosphorylation by piperonylic acid was increased by 1.8 fold compared to that of the solvent DMSO which is a negative control.

Example 5. Measurement of Cytotoxicity of Piperonylic Acid by Concentration

The cytotoxicity of piperonylic acid was measured using HaCaT cells which are keratinocytes. When cells are treated with a yellow water-soluble substrate MTT tetrazolium, the substrate is reduced to MTT formazan by mitochondrial enzymes and the color changes to blue-violet. Since the more living cells there are, the darker the blue-violet color appears, the blue-violet absorbance at 540 nm reflects the concentration of living cells. Specifically, after cells were cultured fully in each well of a 96-well plate, cells were treated with piperonylic acid at a concentration of 0, 25, 50, 100, 250, and 500 μM and cultured at 37° C. in a 5% $CO_2$ incubator for 24 hours and 48 hours, and then the viability of cells was measured by an MTT reagent. A control (0 μM) that had not been treated with piperonylic acid was treated with an equal amount of solvent, DMSO.

Figure 5:
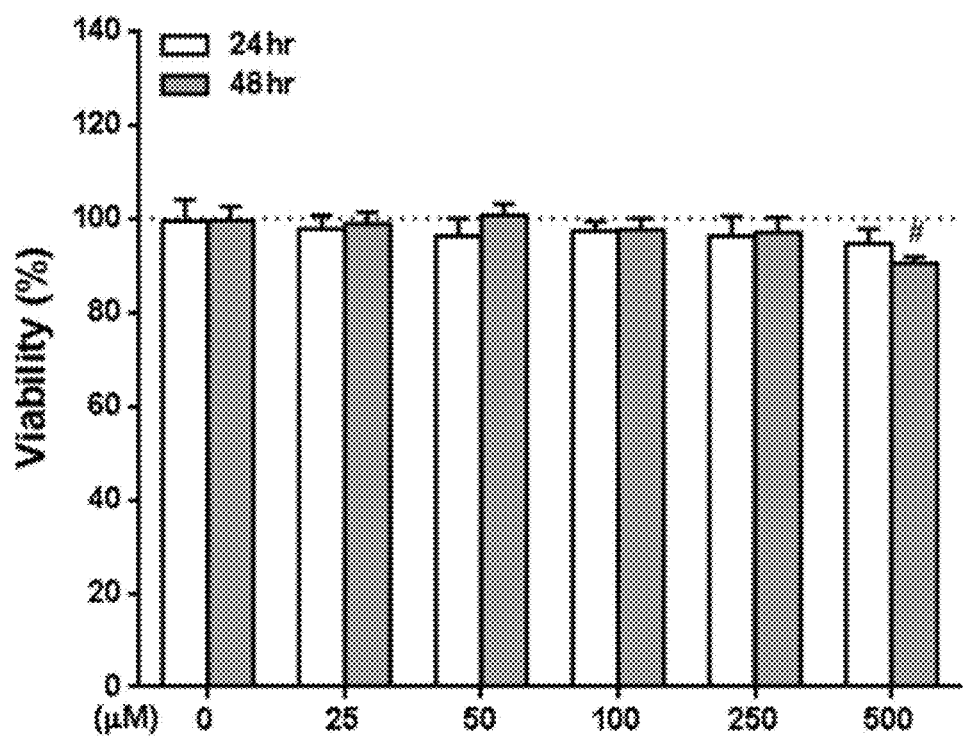
FIG. 5 is a view confirming the cytotoxicity of piperonylic acid at different concentrations on HaCaT cells, which are keratinocytes.

As a result, as illustrated in FIG. 5, a statistically significant difference was shown under the condition of culturing cells at a concentration of 500 μM for 48 hours (#p<0.0001), but since the difference was as small as about 10%, it was confirmed that cytotoxicity to keratinocytes was very low. The significance of the experimental results was verified by performing a t-test on an experimental group and the control.

Example 6. ERK and AKT Activation by Piperonylic Acid

It is well known that the activation of extracellular signal-regulated kinase (ERK) and protein kinase B (AKT) are induced by the EGFR activation and transmit signals required for cell growth and survival. Accordingly, as the activation of EGFR by piperonylic acid was verified in Examples 2 and 3, it was determined whether ERK and AKT, the downstream of EGFR, were also activated by piperonylic acid. Specifically, after HaCaT cells were cultured in a serum-free medium, the cells were treated with piperonylic acid at 0, 25, and 100 μM, and then ERK and AKT, which were activated when phsphorylated, were analyzed by Western blotting method. As antibodies, phosphor-site specific antibodies which are labeling factors of activated ERK and AKT and antibodies that measure total ERK and AKT were used, and GAPDH expressed from a housekeeping gene was measured in order to correct the amount of total proteins between lanes.

Figure 6A:
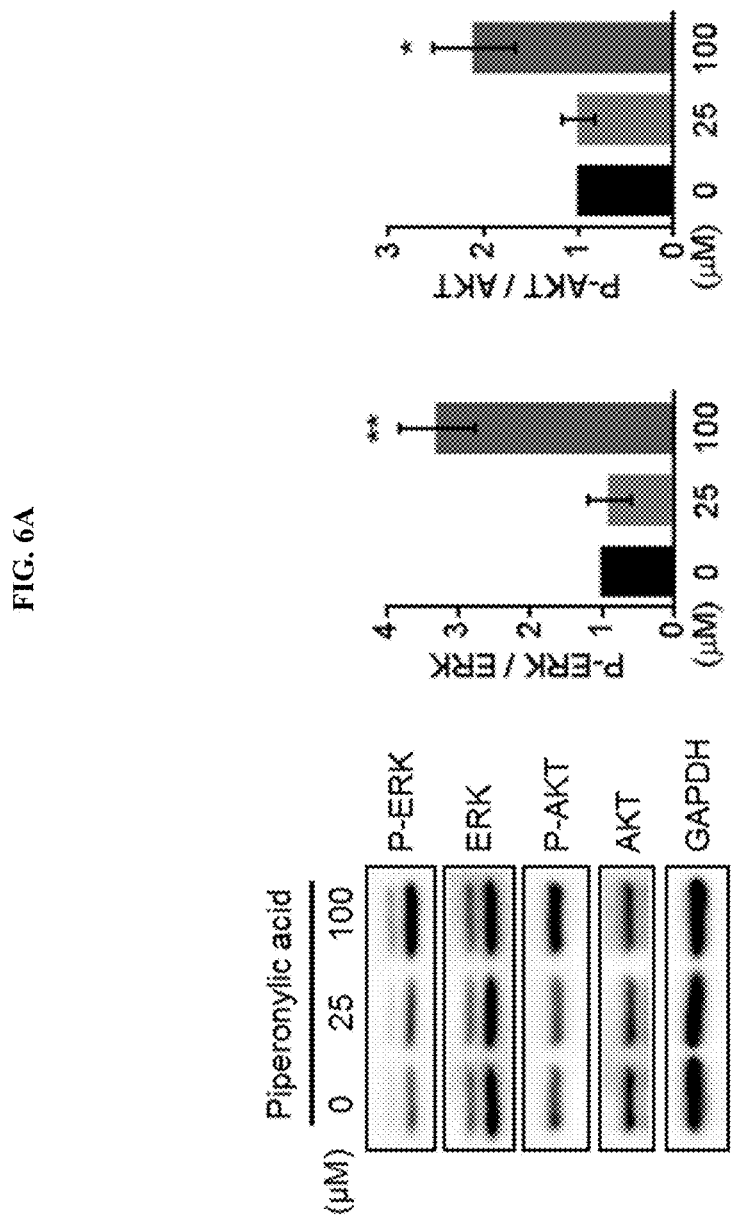
FIG. 6A confirms that ERK and AKT, downstream proteins of EGFR, are activated by piperonylic acid.

As a result, as illustrated in FIG. 6A, it was confirmed that piperonylic acid at 100 μM treatment for 10 minutes sufficiently induced the activation of ERK and AKT. Through three repeated experiments, it was confirmed that piperonylic acid at 100 μM significantly activated ERK and AKT by 3.3 fold and 2.1 fold, respectively compared to the control (t-test, **p<0.01, *p<0.05).

Subsequently, in order to confirm the pattern of ERK and AKT activities by piperonylic acid treatment over time, HaCaT cells cultured in a serum-free medium were treated with piperonylic acid, and then the activity pattern over time was analyzed.

Figure 6B:
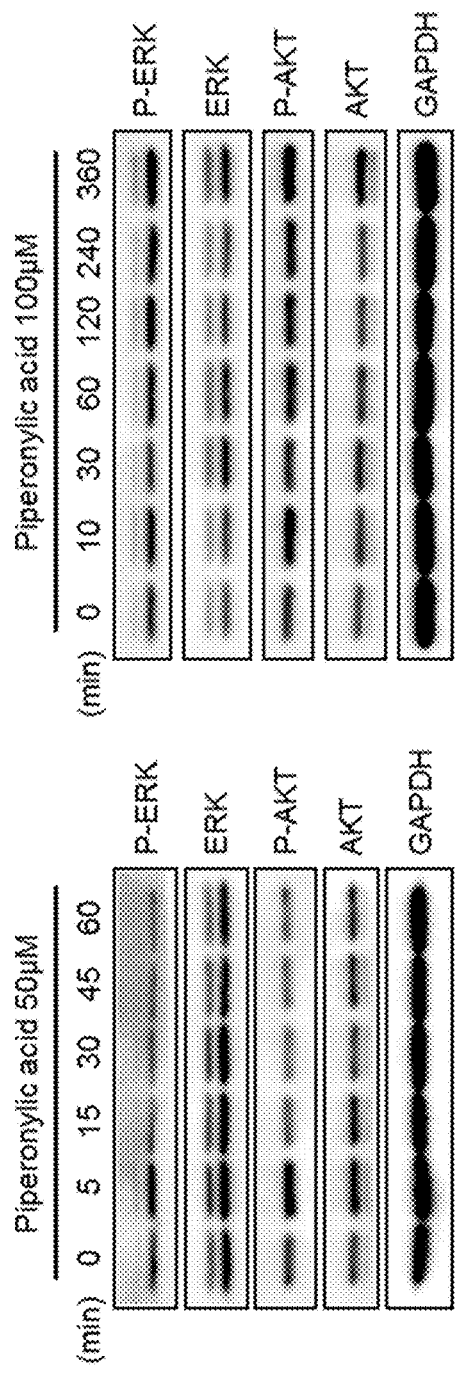
FIG. 6B confirms the pattern of changes in ERK and AKT activities by piperonylic acid over time.

As a result, as illustrated in FIG. 6B, the activation of ERK and AKT was rapidly induced for 5 to 10 minutes, and was immediately down-regulated, and then activated again after 1 to 2 hours.

In order to verify that the activation of ERK and AKT by piperonylic acid were induced by EGFR, the activity of EGFR was suppressed by treating cells with tyrphostin AG1478 which is an EGFR antagonist, and then the activities of ERK and AKT by piperonylic acid were analyzed.

Figure 6C:
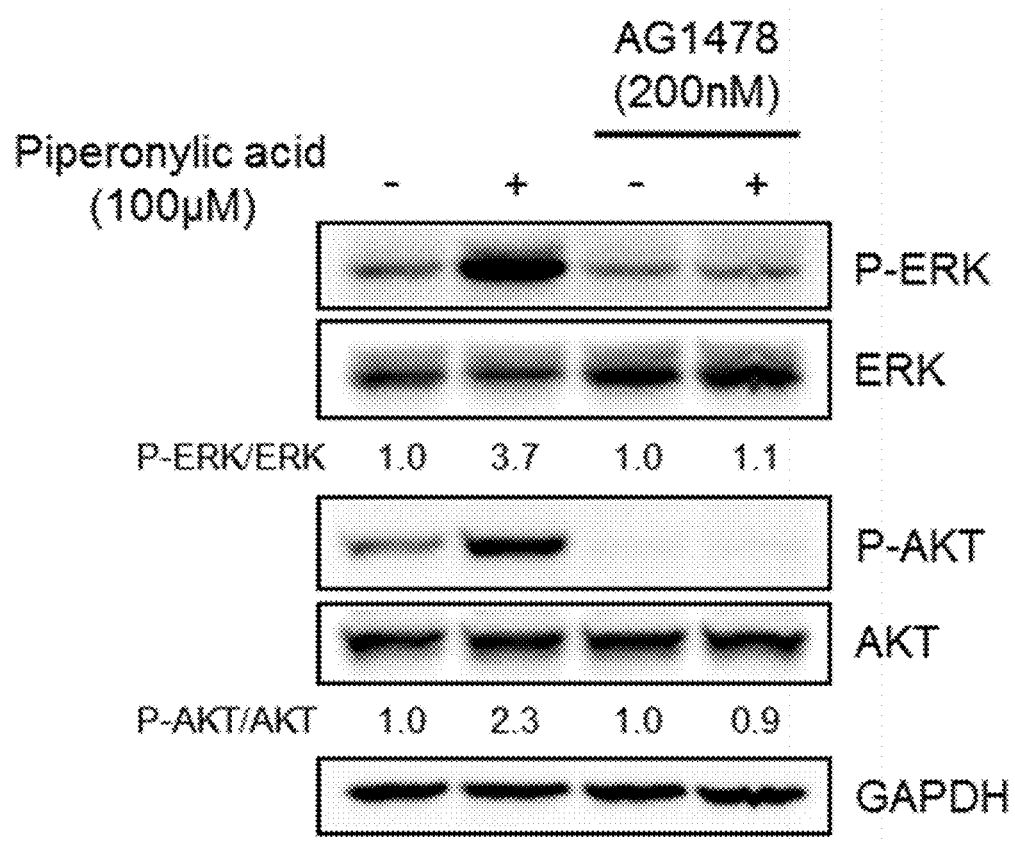
FIG. 6C confirms that ERK and AKT activities due to piperonylic acid depends on EGFR activation.

As a result, as illustrated in FIG. 6C, it was confirmed that when HaCaT cells cultured in a serum-free medium were first treated with AG1478 at 200 nM for 10 minutes, and treated with piperonylic acid, the ERK and AKT were not activated. This reflects that the activation of EGFR by piperonylic acid is required for the activation of ERK and AKT.

Example 7. Change in Gene Expression by Piperonylic Acid

Signaling by EGFR induces gene expression that is important for cell growth and survival via important signaling mediator proteins which are ERK and AKT. It is well known that c-myc, c-jun, c-fos, and egr-1 genes are genes which are regulated by EGFR and promote cell growth and survival. HaCaT cells cultured in a serum-free medium were treated with piperonylic acid at a concentration of 100 μM, which sufficiently induced the activities of ERK and AKT in Example 5, and the changes in expression of each gene were analyzed after 0, 1, 2, and 6 hours. Specifically, a Tri-reagent was used for mRNA extraction, cDNA was made by a reverse transcription polymerase chain reaction (RT-PCR) using a poly-A primer and a reverse transcriptase, and the amount of each mRNA was measured using real-time quantitative PCR. The amount of each mRNA was corrected with the amount of β-actin which is a housekeeping gene.

Figure 7A:
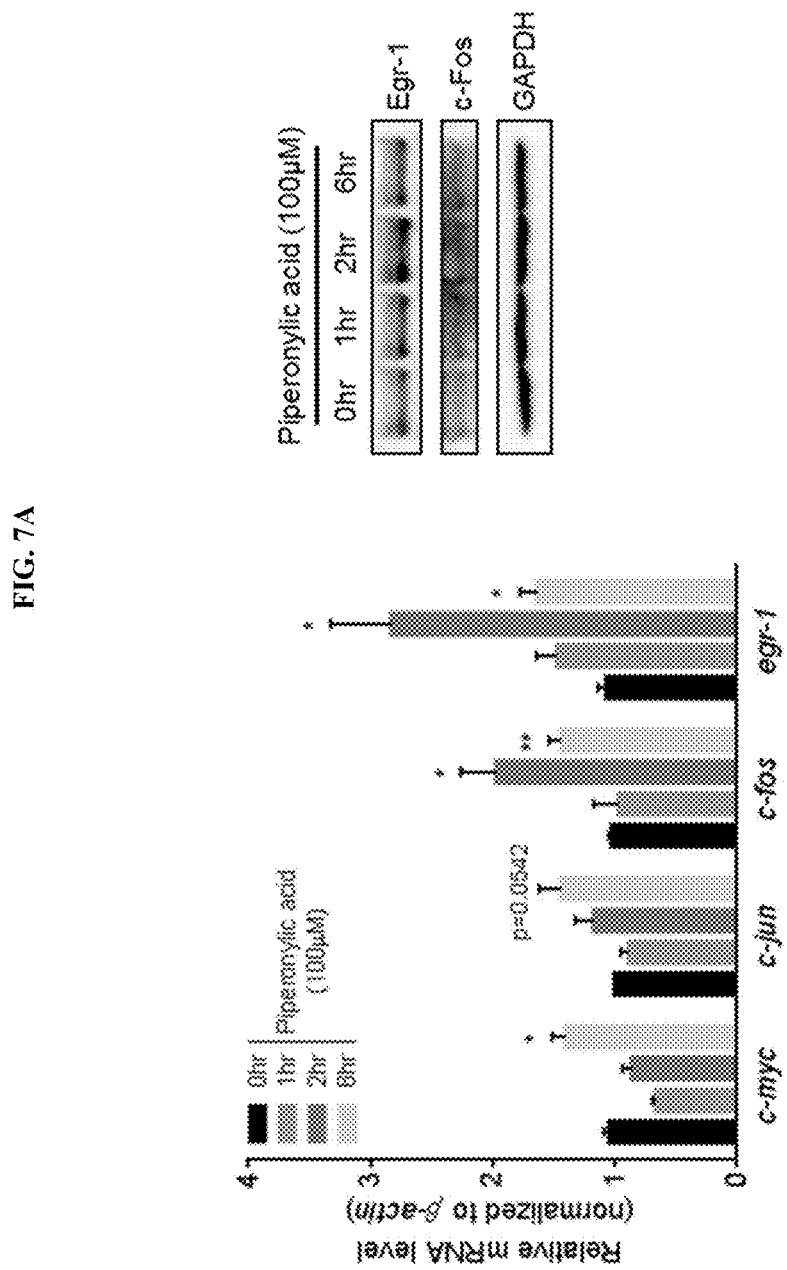
FIG. 7A confirms the pattern of gene expression that changes over time after treatment with piperonylic acid.

As a result, as illustrated in FIG. 7A, c-fos, egr-1, and c-myc exhibited a statistically significant difference at 2 and 6 hours (t-test, *p<0.05, **p<0.01), and c-jun also exhibited an increasing tendency. It was confirmed that the pattern of an increase in expression of the mRNA led to an increase in expression of Egr-1 and c-Fos proteins.

In order to verify that c-fos and egr-1 exhibiting the most remarkable increasing pattern at 2 hours after the treatment with piperonylic acid are affected when the activation of EGFR is suppressed by AG1478 which is an EGFR antagonist, the gene expressions of cells treated with AG1478 and then treated with piperonylic acid and cells treated with only piperonylic acid other than AG1478 were compared, and the expression of proteins were compared using Western blotting method.

Figure 7B:
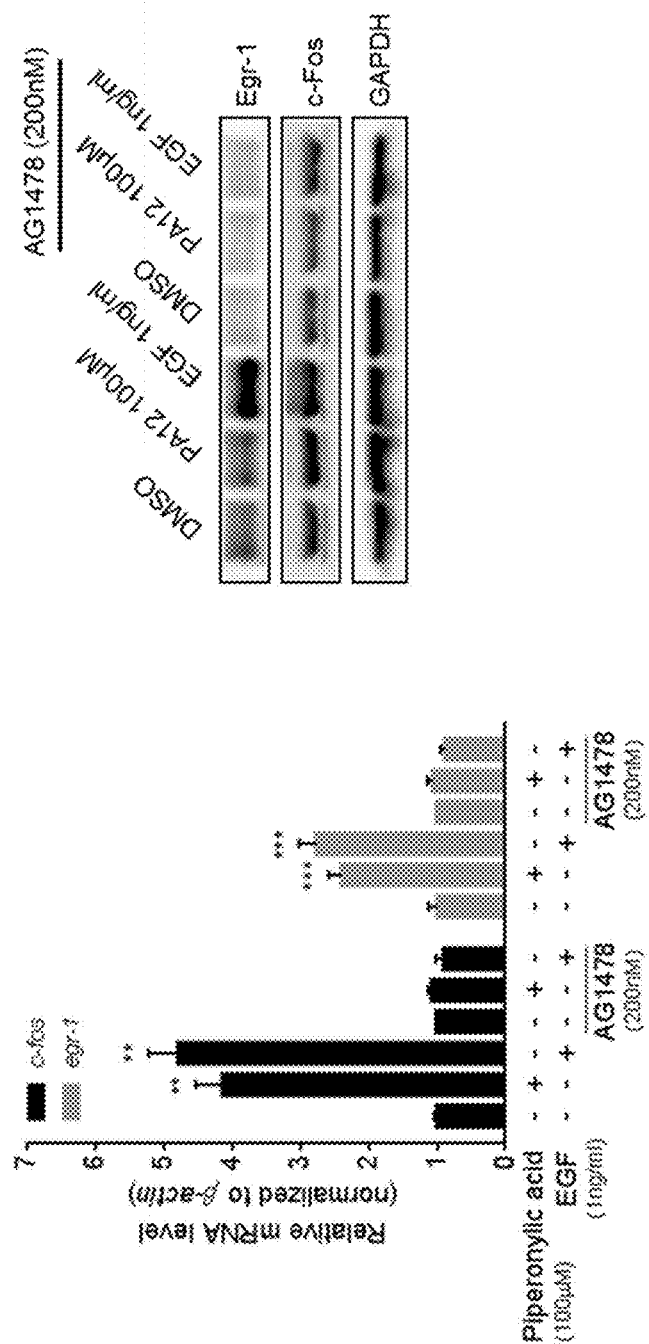
FIG. 7B confirms that the expression of c-fos and egr-1 increased by piperonylic acid depends on EGFR activation.

As a result, as illustrated in FIG. 7B, it was confirmed that the gene expression of c-fos and egr-1 increased by piperonylic acid at 100 µM was completely suppressed by AG1478 (t-test, p<0.01, *p<0.001). Further, it was confirmed that the suppression the gene expression led to a change in protein expression.

Example 8. Promotion of Growth and Proliferation of Keratinocytes by Piperonylic Acid Cell counting kit-8 (CCK-8) is a water-soluble tetrazolium salt reagent called WST-8, and forms orange water-soluble formazan by a dehydrogenase in the mitochondria of living cells. The absorbance of the orange wavelength at 450 nm as indicated by CCK-8 reflects the number of cells, and thus has been used to measure cell growth and proliferation. The growth promotion efficacy of keratinocytes, HaCaT cells, was measured by CCK-8 assay using non-cytotoxic piperonylic acid at a concentration of 50 µM and 100 µM. Specifically, after $1 \times 10^4$ HaCaT cells were cultured on a 96-well plate for 24 hours, growth factors in the medium were removed by exchanging the medium with a serum-free medium, and then the cells were treated with piperonylic acid. An equal amount of the solvent DMSO was used as a negative control, and EGF at a concentration of 1 ng/ml was used as a positive control. After the cells were cultured for 24 hours, the cell growth was analyzed by treating the cells with CCK8 and measuring the absorbance at 450 nm.

Figure 8A:
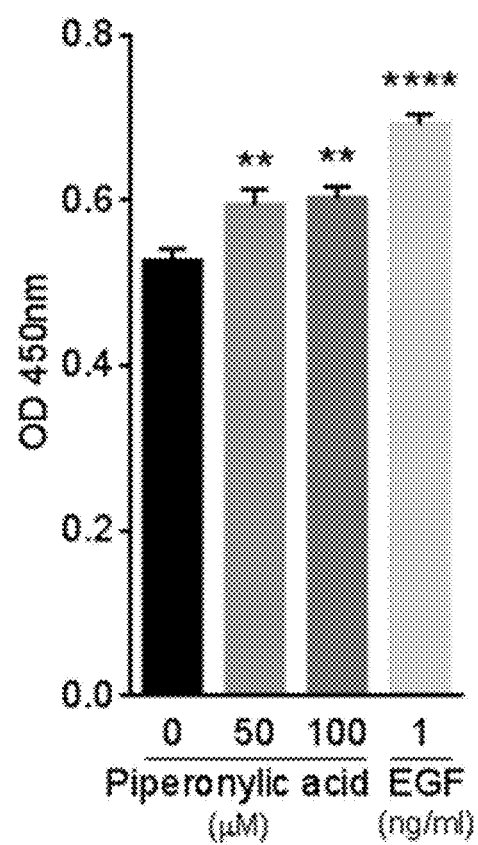
FIG. 8A confirms the growth promotion efficacy of keratinocytes by piperonylic acid through CCK-8 assay.

As a result, as illustrated in FIG. 8A, it was confirmed that when cells were treated with piperonylic acid, cell growth and proliferation were significantly increased compared to the negative control (p<0.01, **p<0.0001).

Further, the cell growth promotion efficacy by piperonylic acid was confirmed through a wound healing assay. Specifically, after HaCaT cells were cultured fully on a 12-well plate, a wound area was formed using a yellow tip, and the cells were treated with piperonylic acid at 50 µM and 100 µM after exchanging the medium with a serum-free medium. The solvent DMSO was used as a negative control, and 1 ng/ml of EGF was used as a positive control.

Figure 8B:
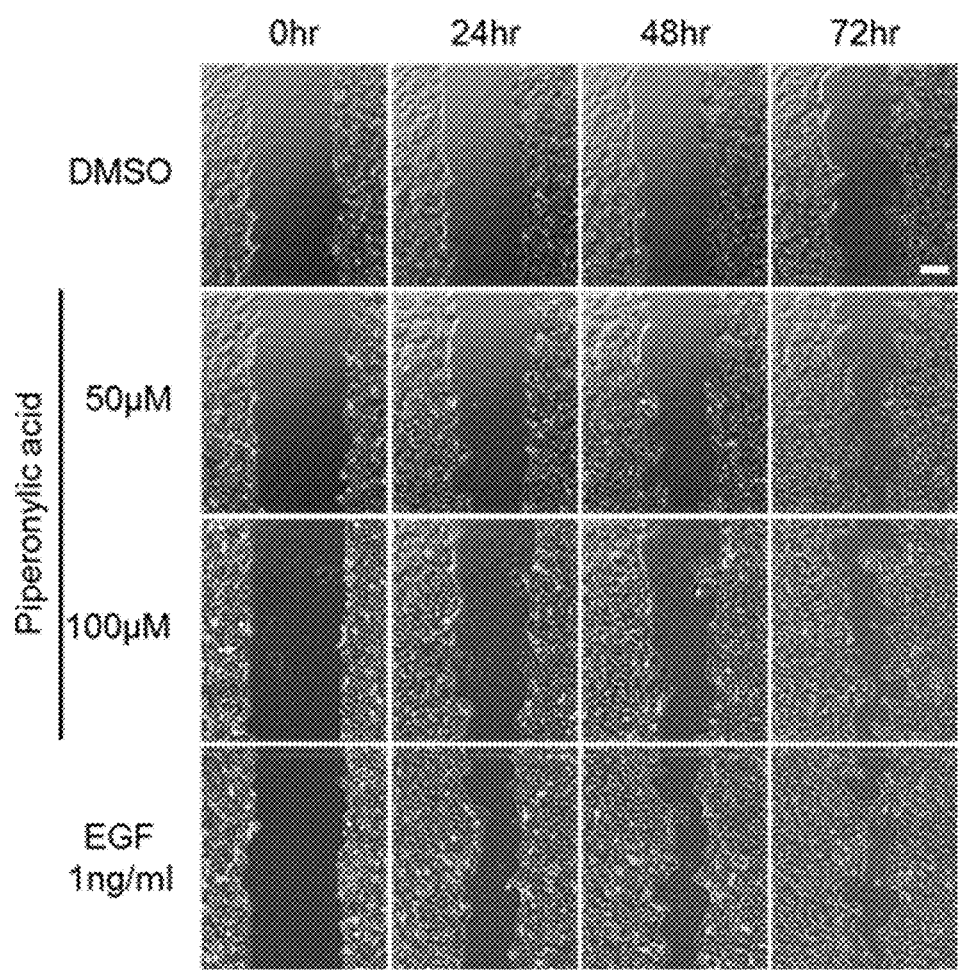
FIGS. 8B and 8C confirm the proliferation and growth promotion efficacy of keratinocytes by piperonylic acid through a wound healing assay.
Figure 8C:
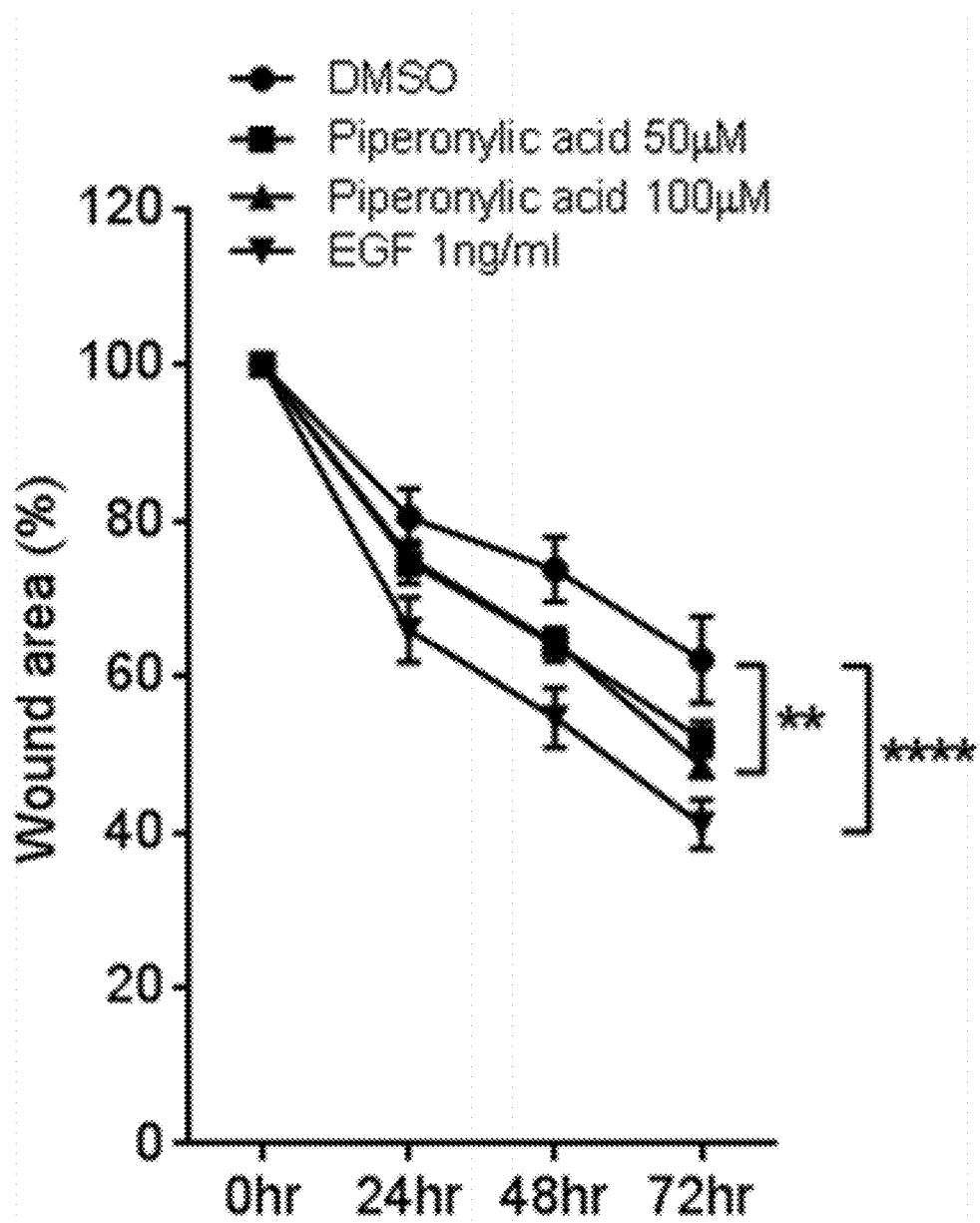

As a result, as illustrated in FIGS. 8B and 8C, it could be confirmed that in the culturing for 3 days, when cells were treated with piperonylic acid, the wound area was more rapidly filled more than the negative control, and on the day 3, a significance was appeared compared to the negative control (Two-way ANOVA, p<0.01, **p<0.0001).

Example 9. Resistance Efficacy of Piperonylic Acid to Ultraviolet Ray (UVB) Stimulus Among the ultraviolet wavelengths, the UVB wavelength corresponding to 280 to 315 nm penetrates the epidermal layer where many keratinocytes are present to cause cell damage. Cell damage caused by UVB may lead to cell apoptosis, and it was confirmed whether piperonylic acid promoted the growth and survival signaling of keratinocytes, and thus exhibited resistance to cell damage induced by UVB. Specifically, the 96-well plate on which $1 \times 10^4$ cells were cultured was irradiated with UVB at 25 mJ/cm², and then the cells were cultured in a serum-free medium in which piperonylic acid or EGF was present. The solvent DMSO was used as a negative control, and cell viability was measured using the CCK-8 method used in Example 7.

Figure 9:
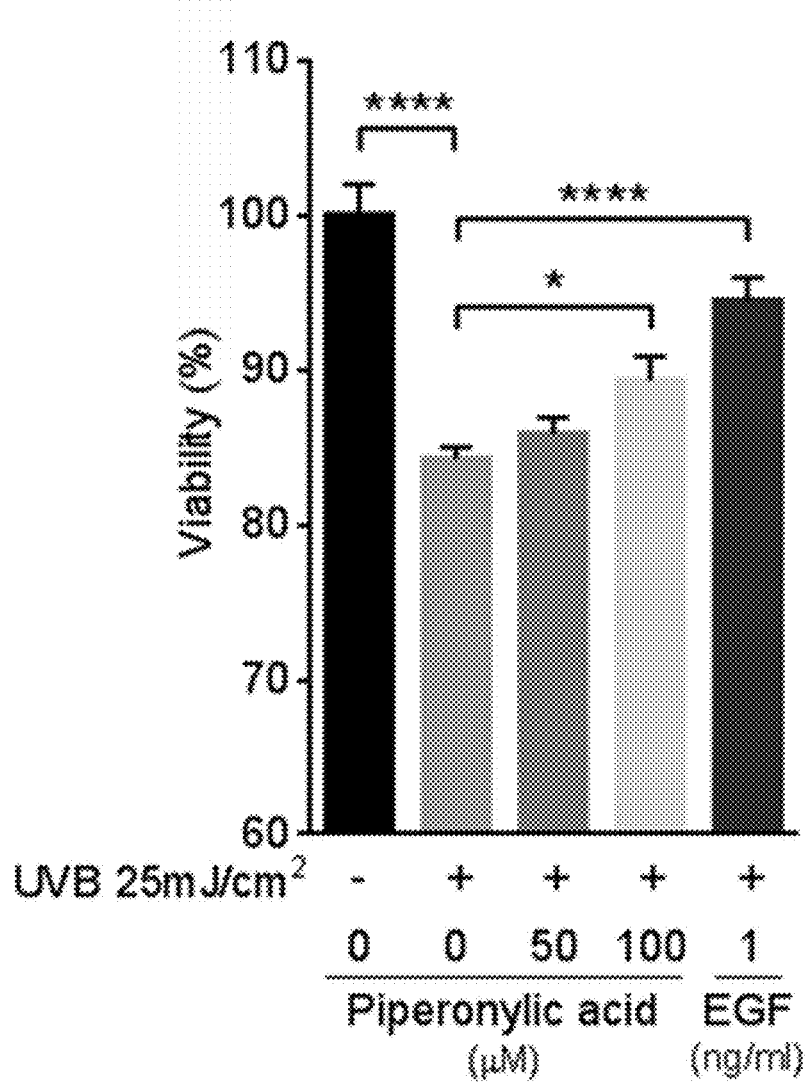
FIG. 9 illustrates that the resistance of keratinocytes is increased by piperonylic acid under conditions of cell damage due to UVB.

As a result, as illustrated in FIG. 9, it was confirmed that in the negative control, cell apoptosis occurred due to UVB at 25 mJ/cm², and thus only 84% of cells survived, whereas 89% of cells survived due to piperonylic acid at 100 µM, exhibiting a statistically significant value (t-test, *p<0.05, ****p<0.0001).

From the results, it can be seen that piperonylic acid can reduce the skin regeneration cycle by promoting the growth and proliferation of keratinocytes, and can have the effect of regenerating the skin such as prevention of skin senescence, enhancement of skin elasticity, and alleviation of skin wrinkles by imparting resistance to stress in the external and/or internal environments.

Although a specific part of the present invention has been described in detail, it will be obvious to a person with ordinary skill in the art to which the present pertains that such a specific description is just a preferred embodiment and the scope of the present invention is not limited thereby. Accordingly, the substantial scope of the present invention will be defined by the appended claims and equivalents thereof.

Figure 10:
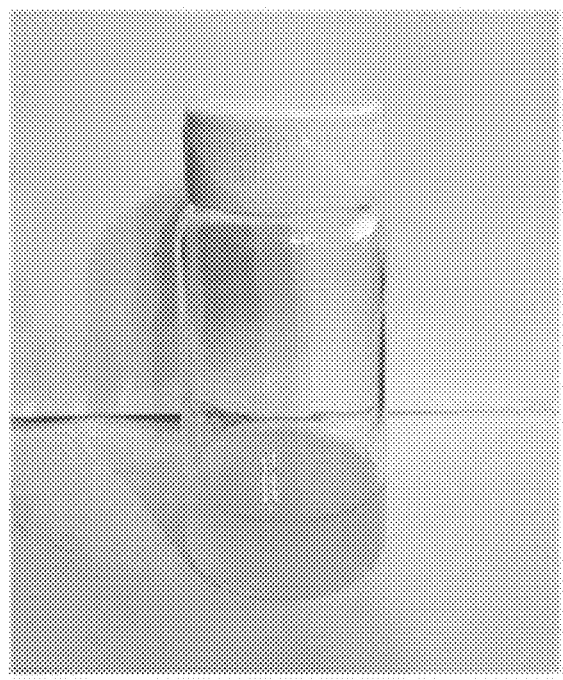
FIG. 10 illustrates a representative photograph of a cosmetic composition preparation for preventing hair loss or promoting hair growth according to the present invention.

Example 10. Preparation of Piperonylic Acid and Compound Comprising the Same The piperonylic acid used in the cell experiment of the present invention for confirmation of hair loss prevention or hair growth promotion effect was purchased from Sigma-Aldrich and used. The composition and composition standard content of the cosmetic composition applied to the human body application test of the present invention are as shown in the following Table 1, and the form thereof is the same as the photograph illustrated in FIG. 10.

TABLE 1

| Component | Content |
| --- | --- |
| Piperonylic acid | 0.1 wt % |
| Carbomer | 0.5 wt % |
| Octyldodeceth-16 | 0.4 wt % |
| Butylene glycol | 5 wt % |
| 1,2-hexanediol | 9 wt % |
| Ethanol | 10 wt % |
| Purified water | The balance |

Example 11. Confirmation of Cell Proliferation Effect on Dermal Papilla Cells Related to Androgenic Alopecia The dermal papilla cells related to androgenic alopecia used in the experiment were a cell line that was immortalized by inserting hTERT and SV40-Tag into dermal papilla cells (DPCs, passage 1) derived from male androgenic alopecia patients, and purchased from Epibiotech Co., Ltd. and used. The proliferation of dermal papilla cells was confirmed using MTT tetrazolium. MTT tetrazolium is reduced to MTT formazan by intracellular mitochondrial enzymes, and at this time, the yellow color turns blue violet. The more cells there are, the stronger the reduction, so a stronger blue violet color appears, and the concentration of living cells is measured by measuring the absorbance of the blue violet color at 540 nm. Specifically, $1 \times 10^4$ cells are aliquoted into 96-well cell culture plates and cultured for 24 hours. Thereafter, a serum-free medium was treated with 50 µM piperonylic acid, and then cultured for 24 hours. Then, after the cells were treated with the MTT reagent for 2 hours, cell growth was analyzed by adding DMSO thereto and confirming the color development at 540 nM. A solvent DMSO was used as a negative control.

As a result, it was confirmed that the treatment with piperonylic acid promoted cell proliferation of dermal papilla cells related to androgenic alopecia (FIG. 11).

In addition, in order to investigate a gene expression pattern involved in the proliferation of dermal papilla cells related to androgenic alopecia, the human dermal papilla cells were cultured in a serum-free medium for 24 hours, and then treated with 25 and 50 μM piperonylic acid, respectively. The cells were treated with a drug, and after 24 hours, the levels of cyclin D were analyzed by the western blotting method. As an antibody, GAPDH, which is always expressed constantly, was used to correct the total protein amount between the cyclin D antibody and each lane. A solvent DMSO was used as a negative control.

As a result, it was confirmed that the expression of cyclin D protein involved in cell proliferation in androgenic alopecia-related dermal papilla cells treated with piperonylic acid was significantly increased compared to the control (FIG. 12).

Meanwhile, in order to investigate the proliferation pattern of dermal papilla cells related to androgenic alopecia during treatment with piperonylic acid, a 12-well cell culture plate was fully filled with the dermal papilla cells, and the cells were injured using a yellow tip. Thereafter, cell growth promoting efficacy was observed at 24 hours and 48 hours after treatment with 100 μM piperonylic acid in a serum-free medium. A solvent DMSO was used as a negative control.

As a result, it was again confirmed that the treatment with piperonylic acid promoted cell proliferation of dermal papilla cells related to androgenic alopecia (FIG. 13).

Example 12. Confirmation of Hair Loss Prevention or Hair Growth Promoting Effect Through Human Body Application Test Since hair loss is a symptom that appears due to the interaction of various types of cells that make up hair cells, in addition to the cell proliferation promoting effect of dermal papilla cells confirmed in Example 11, it was confirmed through a human body application test whether piperonylic acid has an effect of preventing hair loss or promoting hair growth when actually applied to the human body.

Specifically, for male subjects (3 or more) showing androgenic alopecia symptoms, the cosmetic composition (hair tonic containing 0.1% piperonylic acid) prepared in the Example 10 was applied to the skin once a day for 12 weeks. The subjects were instructed to apply 2 mL each of the cosmetic composition to a scalp site where the hair was lacking in the absence of moisture on the scalp.

After a 12-week human body application test, a panel of experts evaluated clinical photographs, and as a result, the piperonylic acid-containing composition of the present invention showed skin safety and skin absorption applicable to cosmetics. Furthermore, all the subjects showed a feeling of satisfaction as their hair generally became thick and healthy, and elastic, and the overall volume was strengthened.

In order to quantify the results of the human body application test, the hair conditions (hair count per 25 mm$^2$) of 3 male patients with androgenic alopecia at 0, 6 and 12 weeks were quantified in FIG. 15, and it was confirmed that there was a statistically significant effect of preventing hair loss or promoting hair growth (p<0.02).

In conclusion, it can be seen that the cosmetic composition comprising piperonylic acid according to the present invention can be usefully utilized for preventing hair loss or promoting hair growth, specifically for improving hair health and alleviating androgenic alopecia symptoms.

INDUSTRIAL APPLICABILITY

Piperonylic acid of the present invention is a natural material that can be obtained from the extract of various plant species, and performs a similar function to epidermal growth factor (EGF), and thus is expected to be used in applications in various fields including medicines, quasi-drugs, cosmetics, cosmetic substances, functional biomaterials, and functional food materials in order to prevent skin senescence and damage due to exogenous or endogenous factors or treat skin wounds.

In addition, piperonylic acid of the present invention can be usefully used in cosmetics, drugs, quasi-drugs, foods, and the like for preventing hair loss or promoting hair growth.

The invention claimed is:

1. A method of treating hair loss or promoting hair growth, the method comprising administering a composition comprising an effective amount of piperonylic acid represented by the following Chemical Formula 1 to a subject in need thereof

[Chemical Formula 1]

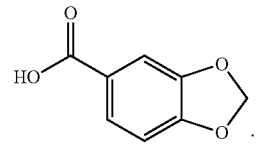

2. The method of claim 1, wherein the composition is cosmetic composition, pharmaceutical composition, or food composition.

3. The method of claim 1, wherein the piperonylic acid is derived from natural products or chemically synthesized.

4. The method of claim 1, wherein the piperonylic acid has one or more hair health improvement uses selected from the group consisting of an increase in hair thickness, an improvement in hair elasticity, an improvement in hair volume, and an increase in hair count.

5. The method of claim 1, wherein the piperonylic acid alleviates androgenic alopecia symptoms.

6. The method of claim 1, wherein the piperonylic acid promotes the proliferation of dermal papilla cells.

7. The method of claim 1, wherein the composition comprises piperonylic acid in an amount of 0.005 wt % to 5 wt % based on the composition.

8. The method of claim 2, wherein the cosmetic composition comprises one or more cosmetically acceptable additives or carriers.

9. The method of claim 2, wherein the cosmetic composition is one or more formulations selected from the group consisting of hair tonic, hair conditioner, hair essence, hair lotion, hair nourishing lotion, hair shampoo, hair rinse, hair treatment, hair cream, hair nourishing cream, hair moisturizing cream, hair massage cream, hair wax, hair aerosol, hair pack, hair nourishing pack, hair soap, hair cleansing foam, hair oil, hair drying agent, hair preservation treatment agent, hair colorant, hair waving preparation, hair decolorant, hair gel, hair glaze, hair dressing agent, hair lacquer, hair moisturizer, hair mousse and hair spray.

10. The method of claim 2, wherein the pharmaceutical composition is one or more external skin application selected from the group consisting of an aerosol, an ointment, a liquid, a lotion, a patch, an application powder, an oil, a cream and a gel.

* * * * *